US005420025A

United States Patent [19]

Takagi et al.

[11] Patent Number: 5,420,025
[45] Date of Patent: May 30, 1995

[54] RECOMBINANT TRANSGLUTAMINASE

[75] Inventors: Hiroshi Takagi; Shino Arafuka; Hiroshi Matsui, all of Kanagawa; Kinya Washizu, Ibaraki; Keiichi Ando, Ibaraki; Satoshi Koikeda, Ibaraki, all of Japan

[73] Assignees: Amano Pharmaceutical Co., Ltd., Aichi; Ajinomoto Co., Inc., Tokyo, both of Japan

[21] Appl. No.: 136,993

[22] Filed: Oct. 18, 1993

Related U.S. Application Data

[63] Continuation of Ser. No. 777,447, Oct. 18, 1991, abandoned.

[30] Foreign Application Priority Data

Oct. 19, 1990 [JP] Japan ................................ 2-282566

[51] Int. Cl.$^6$ .......................... C12N 9/10; C12N 15/54; C12N 15/63; C12N 15/66
[52] U.S. Cl. .................................. 435/193; 435/69.1; 435/252.3; 435/254.21; 435/252.33; 435/252.35; 536/23.2
[58] Field of Search ................. 435/69.1, 172.3, 320.1, 435/193, 252.3, 254.21, 252.35, 252.33; 536/23.2, 24.1, 25.3

[56] References Cited

U.S. PATENT DOCUMENTS 5,156,956 10/1992 Motoki ............................... 435/68.1

FOREIGN PATENT DOCUMENTS 0379606 8/1990 European Pat. Off. .
0441353 8/1991 European Pat. Off. .
8907398 8/1989 WIPO .

OTHER PUBLICATIONS

Cloning of Physarum Actin Sequences in an Exonuclease-Deficient Bacterial Host, Nader, W. F. et al, Proc. Natl. Acad. Sci. U.S.A., 82: 2698–2702 (1985).
Propagation of Some Human DNA Sequences in Bacteriophage λ Vectors Requires *Mutant Escherichia coli* Hosts, Wyman, A. R. et al., Proc. Natl. Acad. Sci. U.S.A., 82: 2880–2884 (1985).
Kilo-Sequencing: Creation of an Ordered Nest of Asymmetric Deletions Across a Large Target Sequence Carried on Phage M13, Barnes, W. M. et al., Methods in Enzymology 101: 98–122 (1983).
Sequence Diversity Among Related Genes for Recognitionf Specific Targets in DNA Molecules, Gough, J. A. et al., J. Mol. Biol., 166: 1–19 (1983).
Improvement of the Dideoxy Chain Termination Method of DNA Sequencing By Use of Deoxy-7-Deazagunanosine Triphosphate in Place of dGTP, Mizusawa, S. et al., Nucleic Acids Res., 14: 1319–1324 (1986).
ssDNA Binding Proteins, Chase, J. W. et al., Ann. Rev. Biochem., 55: 118–119 (1986).
H. Ando et al., "Purification and characteristics of a Novel Transglutaminase derived from microorganisms", Oct. 1989, pp. 2613–2617 (Agric. Biol. Chem., vol. 53, No. 10).
E. Rajpert-De Meyts et al, "Cloning and nucleotide sequence of human gamma-glutamyl transpeptidase", Dec. 1988, pp. 8840–8844 (Proc. of the Nat. Acad. of Sciences of the USA, vol. 85, No. 23).
Edwin C. Webb, Enzyme Nomenclature 1984, Recommendations of the Nomenclature Committee of the International Union of Biochemistry of the Nomenclature and Classification of Enzyme-Catalysed Reactions, pp. 175–177.
Lee, C. C. et al. *Science* 239:1288–1291 (1988).

*Primary Examiner*—Robert A. Wax
*Assistant Examiner*—Dian C. Jacobson
*Attorney, Agent, or Firm*—Sughrue, Mion, Zinn, Macpeak & Seas

[57] ABSTRACT

A DNA gene which encodes transglutaminase, a plasmid in which the DNA gene is incorporated, a transformant transformed with the plasmid and a process for the production of transglutaminase that comprises culturing the transformant.

22 Claims, 1 Drawing Sheet

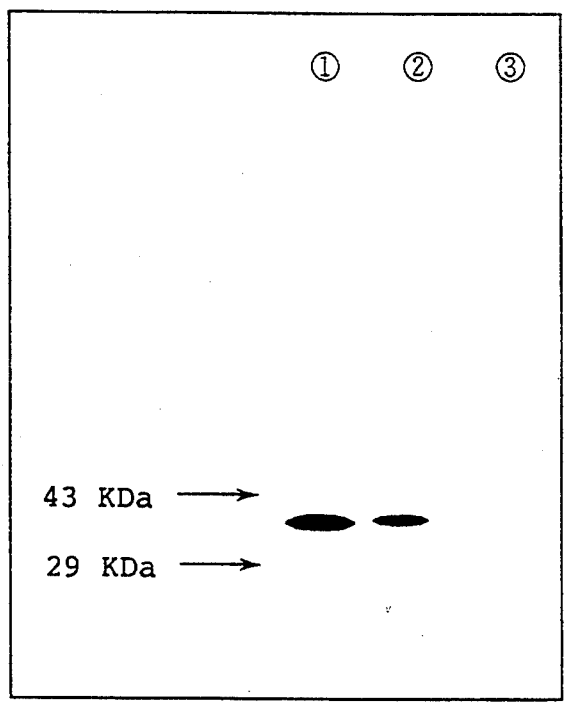

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 331 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Glu Lys Gly Phe Gln Arg Ala Arg Glu
            115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
            195                 200                 205

Ser Ser Ser Ala Asp Lys Arg Lys Tyr Gly Asp Pro Asp Ala Phe Arg
    210                 215                 220
```

```
    Pro Ala Pro Gly Thr Gly Leu Val Asp Met Ser Arg Asp Arg Asn Ile
    225                 230                 235                 240

Pro Arg Ser Pro Thr Ser Pro Gly Glu Gly Phe Val Asn Phe Asp Tyr
                    245                 250                 255

Gly Trp Phe Gly Ala Gln Thr Glu Ala Asp Ala Asp Lys Thr Val Trp
                260                 265                 270

Thr His Gly Asn His Tyr His Ala Pro Asn Gly Ser Leu Gly Ala Met
            275                 280                 285

His Val Tyr Glu Ser Lys Phe Arg Asn Trp Ser Glu Gly Tyr Ser Asp
        290                 295                 300

Phe Asp Arg Gly Ala Tyr Val Ile Thr Phe Ile Pro Lys Ser Trp Asn
    305                 310                 315                 320

Thr Ala Pro Asp Lys Val Lys Gln Gly Trp Pro
                    325                 330
```

(2) INFORMATION FOR SEQ ID NO:2:

(i) SEQUENCE CHARACTERISTICS:
        (A) LENGTH: 993 base pairs
        (B) TYPE: nucleic acid
        (C) STRANDEDNESS: double
        (D) TOPOLOGY: linear (ii) MOLECULE TYPE: Other nucleic acid (synthetic DNA)

(xi) SEQUENCE DESCRIPTION: SEQ ID NO:2:

```
GATTCTGATG ACAGAGTCAC TCCACCAGCT GAACCATTGG ATAGAATGCC AGATCCATAC      60
AGACCATCTT ACGGTAGAGC TGAAACTGTT GTCAACAACT ACATTAGAAA GTGGCAACAA     120
GTCTACTCTC ACAGAGATGG TAGAAAGCAA CAAATGACTG AAGAACAAAG AGAATGGTTG     180
TCTTACGGTT GTGTTGGTGT TACTTGGGTT AACTCTGGTC AATACCCAAC TAACAGATTG     240
GCTTTCGCTT CTTTCGATGA AGATAGATTC AAGAACGAAT TGAAGAACGG TAGACCAAGA     300
TCCGGTGAAA CTAGAGCTGA ATTCGAAGGT AGAGTTGCTA AGGAATCTTT CGATGAAGAA     360
AAGGGTTTCC AAAGAGCTAG AAGTTGCT TCTGTTATGA ACAGAGCTCT AGAAAACGCT     420
CACGATGAAT CTGCTTACTT GGATAACTTG AAGAAGGAAT TGGCCAACGG TAACGATGCT     480
TTGAGAAACG AAGATGCTAG ATCCCCATTC TACTCTGCTT TGAGAAACAC TCCATCTTTC     540
AAGGAAAGAA ACGGTGGTAA CCACGATCCA TCCAGAATGA AGGCTGTTAT TTACTCTAAG     600
CACTTCTGGT CTGGTCAAGA TAGATCTTCT TCTGCTGATA AGAGAAAGTA CGGTGATCCA     660
GATGCTTTCA GACCAGCTCC AGGTACCGGT TTGGTCGACA TGTCCAGAGA TAGAAACATT     720
CCAAGATCCC CAACTTCTCC AGGTGAAGGT TTCGTCAACT TCGATTACGG TTGGTTCGGT     780
GCTCAAACTG AAGCTGATGC TGATAAGACT GTTTGGACCC ATGGTAACCA CTACCACGCT     840
CCAAACGGTT CTTTGGGTGC TATGCACGTC TACGAATCTA AGTTCAGAAA CTGGTCTGAA     900
GGTTACTCTG ATTTCGATAG AGGTGCTTAC GTTATTACTT TCATTCCAAA GTCTTGGAAC     960
ACTGCTCCAG ACAAGGTCAA GCAAGGTTGG CCA                                   993
```

(2) INFORMATION FOR SEQ ID NO:3:

(i) SEQUENCE CHARACTERISTICS:
        (A) LENGTH: 993 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

-continued

```
GACTCCGACG ACAGGGTCAC CCCTCCCGCC GAGCCGCTCG ACAGGATGCC CGACCCGTAC      60
CGTCCCTCGT ACGGCAGGGC CGAGACGGTC GTCAACAACT ACATACGCAA GTGGCAGCAG     120
GTCTACAGCC ACCGCGACGG CAGGAAGCAG CAGATGACCG AGGAGCAACG GGAGTGGCTG     180
TCCTACGGCT GCGTCGGTGT CACCTGGGTC AATTCGGGTC AGTACCCCAC GAACAGACTG     240
GCCTTCGCGT CCTTCGACGA GGACAGGTTC AAGAACGAGC TGAAGAACGG CAGGCCCCGG     300
TCCGGCGAGA CGCGGGCGGA GTTCGAGGGC CGCGTCGCGA AGGAGAGCTT TGATGAAGAG     360
AAGGGGTTCC AGCGGGCGCG TGAGGTGGCG TCCGTGATGA CAGGGCCCT  GGAGAACGCC     420
CACGACGAGA GCGCTTACCT CGACAACCTC AAGAAGGAAC TGGCGAACGG CAACGACGCC     480
CTGCGCAACG AGGACGCCCG TTCCCCGTTC TACTCGGCGC TGCGGAACAC GCCGTCCTTT     540
AAGGAGCGGA ACGGAGGCAA TCACGACCCG TCCAGGATGA AGGCCGTCAT CTACTCGAAG     600
CACTTCTGGA GCGGCCAGGA CCGGTCGAGT TCGGCCGACA GAGGAAGTA CGGCGACCCG      660
GACGCTTTCC GCCCGGCCCC CGGGACCGGC CTGGTCGACA TGTCGAGGGA CAGGAACATT     720
CCGCGCAGCC CCACCAGCCC CGGTGAGGGA TTCGTCAATT TCGACTACGG CTGGTTCGGC     780
GCCCAGACGG AAGCGGACGC CGACAAGACC GTCTGGACCC ACGGAAATCA CTATCACGCG     840
CCCAATGGCA GCCTTGGTGC CATGCATGTA TACGAGAGCA AGTTCCGCAA CTGGTCCGAA     900
GGTTACTCCG ACTTCGACCG CGGAGCCTAT GTGATCACCT TCATCCCCAA GAGCTGGAAC     960
ACCGCCCCCG ACAAGGTAAA GCAGGGCTGG CCG                                  993
```

(2) INFORMATION FOR SEQ ID NO:4:

(i) SEQUENCE CHARACTERISTICS:
(A) LENGTH: 75 amino acids
(B) TYPE: amino acid
(D) TOPOLOGY: linear (ii) MOLECULE TYPE: protein (xi) SEQUENCE DESCRIPTION: SEQ ID NO:4:

```
Met Arg Tyr Thr Pro Glu Ala Leu Val Phe Ala Thr Met Ser Ala Val
-75              -70                 -65                 -60

Tyr Ala Pro Pro Asp Ser Cys Arg Arg Pro Ala Arg Pro Pro Thr
                -55              -50                 -45

Met Ala Arg Gly Lys Arg Arg Ser Pro Thr Pro Lys Pro Thr Ala Ser
            -40              -35              -30

Arg Arg Met Thr Ser Arg His Gln Arg Ala Gln Arg Ser Ala Pro Ala
        -25              -20              -15

Ala Ser Ser Ala Gly Pro Ser Phe Arg Ala Pro
    -10              -5
```

(2) INFORMATION FOR SEQ ID NO:5:

(i) SEQUENCE CHARACTERISTICS:
(A) LENGTH: 39 amino acids
(B) TYPE: amino acid
(D) TOPOLOGY: linear (ii) MOLECULE TYPE: peptide (xi) SEQUENCE DESCRIPTION: SEQ ID NO:5:

```
Lys Arg Arg Ser Pro Thr Pro Lys Pro Thr Ala Ser Arg Arg Met Thr
-39              -35              -30                 -25

Ser Arg His Gln Arg Ala Gln Arg Ser Ala Pro Ala Ala Ser Ser Ala
            -20              -15              -10

Gly Pro Ser Phe Arg Ala Pro
        -5
```

( 2 ) INFORMATION FOR SEQ ID NO:6:

( i ) SEQUENCE CHARACTERISTICS:
        ( A ) LENGTH: 225 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
ATGCGCTATA CGCCGGAGGC TCTCGTCTTC GCCACTATGA GTGCGGTTTA TGCACCGCCG    60
GATTCATGCC GTCGGCCGGC GAGGCCGCCG CCGACAATGG CGCGGGGGAA GAGACGAAGT   120
CCTACGCCGA AACCTACCGC CTCACGGCGG ATGACGTCGC GACATCAACG CGCTCAACGA   180
AGCGCTCCGG CCGCTTCGAG CGCCGGCCCG TCGTTCCGGG CCCCC                   225
```

( 2 ) INFORMATION FOR SEQ ID NO:7:

( i ) SEQUENCE CHARACTERISTICS:
        ( A ) LENGTH: 117 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( x i ) SEQUENCE DESCRIPTION: SEQ ID NO:7:

```
AAGAGAAGAT CTCCAACTCC AAAGCCAACT GCTTCTAGAA GAATGACTTC TAGACACCAA    60
AGAGCTCAAA GATCTGCTCC AGCTGCTTCT TCTGCTGGTC CATCTTTCAG AGCTCCA     117
```

( 2 ) INFORMATION FOR SEQ ID NO:8:

( i ) SEQUENCE CHARACTERISTICS:
        ( A ) LENGTH: 1218 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

```
ATGCGCTATA CGCCGGAGGC TCTCGTCTTC GCCACTATGA GTGCGGTTTA TGCACCGCCG    60
GATTCATGCC GTCGGCCGGC GAGGCCGCCG CCGACAATGG CGCGGGGGAA GAGACGAAGT   120
CCTACGCCGA AACCTACCGC CTCACGGCGG ATGACGTCGC GACATCAACG CGCTCAACGA   180
AGCGCTCCGG CCGCTTCGAG CGCCGGCCCG TCGTTCCGGG CCCCGACTC CGACGACAGG    240
GTCACCCCTC CGCCGAGCC GCTCGACAGG ATGCCCGACC CGTACCGTCC CTCGTACGGC    300
AGGGCCGAGA CGGTCGTCAA CAACTACATA CGCAAGTGGC AGCAGGTCTA CAGCCACCGC   360
GACGGCAGGA AGCAGCAGAT GACCGAGGAG CAACGGGAGT GGCTGTCCTA CGGCTGCGTC   420
GGTGTCACCT GGGTCAATTC GGGTCAGTAC CCCACGAACA GACTGGCCTT CGCGTCCTTC   480
GACGAGGACA GGTTCAAGAA CGAGCTGAAG AACGGCAGGC CCGGTCCGG CGAGACGCGG    540
GCGGAGTTCG AGGGCCGCGT CGCGAAGGAG AGCTTTGATG AAGAGAAGGG GTTCCAGCGG   600
GCGCGTGAGG TGGCGTCCGT GATGAACAGG GCCCTGGAGA ACGCCACGA CGAGAGCGCT    660
TACCTCGACA ACCTCAAGAA GGAACTGGCG AACGGCAACG ACGCCCTGCG CAACGAGGAC   720
GCCCGTTCCC CGTTCTACTC GGCGCTGCGG AACACGCCGT CCTTTAAGGA GCGGAACGGA   780
GGCAATCACG ACCCGTCCAG GATGAAGGCC GTCATCTACT CGAAGCACTT CTGGAGCGGC   840
CAGGACCGGT CGAGTTCGGC CGACAAGAGG AAGTACGGCG ACCCGGACGC TTTCCGCCCG   900
GCCCCCGGGA CCGGCCTGGT CGACATGTCG AGGGACAGGA ACATTCCGCG CAGCCCCACC   960
```

| | | | | | |
|---|---|---|---|---|---|
| AGCCCCGGTG | AGGGATTCGT | CAATTTCGAC | TACGGCTGGT | TCGGCGCCCA | GACGGAAGCG | 1020
| GACGCCGACA | AGACCGTCTG | GACCCACGGA | AATCACTATC | ACGCGCCCAA | TGGCAGCCTT | 1080
| GGTGCCATGC | ATGTATACGA | GAGCAAGTTC | CGCAACTGGT | CCGAAGGTTA | CTCCGACTTC | 1140
| GACCGCGGAG | CCTATGTGAT | CACCTTCATC | CCCAAGAGCT | GGAACACCGC | CCCCGACAAG | 1200
| GTAAAGCAGG | GCTGGCCG | | | | | 1218

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (synthetic DNA)

(ix) FEATURE:
        (A) NAME/KEY: modifiedbase
        (B) LOCATION: 18
        (D) OTHER INFORMATION: /modbase=i (xi) SEQUENCE DESCRIPTION: SEQ ID NO:9:

TTYGAYGARG ARAARGGNTT     20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid (synthetic DNA)

(ix) FEATURE:
        (A) NAME/KEY: modifiedbase
        (B) LOCATION: 6
        (D) OTHER INFORMATION: /modbase=i (ix) FEATURE:
        (A) NAME/KEY: modifiedbase
        (B) LOCATION: 15
        (D) OTHER INFORMATION: /modbase=i (xi) SEQUENCE DESCRIPTION: SEQ ID NO:10:

GGCCANCCYT GYTTNACYTT     20

(2) INFORMATION FOR SEQ ID NO:11:

(i) SEQUENCE CHARACTERISTICS:
        (A) LENGTH: 564 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

| | | | | | |
|---|---|---|---|---|---|
| TCCGTGATGA | ACAGGGCCCT | GGAGAACGCC | CACGACGAGA | GCGCTTACCT | CGACAACCTC | 60
| AAGAAGGAAC | TGGCGAACGG | CAACGACGCC | CTGCGCAACG | AGGACGCCCG | TTCCCCGTTC | 120
| TACTCGGCGC | TGCGGAACAC | GCCGTCCTTT | AAGGAGCGGA | ACGGAGGCAA | TCACGACCCG | 180
| TCCAGGATGA | AGGCCGTCAT | CTACTCGAAG | CACTTCTGGA | GCGGCCAGGA | CCGGTCGAGT | 240
| TCGGCCGACA | AGAGGAAGTA | CGGCGACCCG | GACGCTTTCC | GCCCGGCCCC | CGGGACCGGC | 300
| CTGGTCGACA | TGTCGAGGGA | CAGGAACATT | CCGCGCAGCC | CACCAGCCC | CGGTGAGGGA | 360
| TTCGTCAATT | TCGACTACGG | CTGGTTCGGC | GCCCAGACGG | AAGCGGACGC | CGACAAGACC | 420

```
GTCTGGACCC ACGGAAATCA CTATCACGCG CCCAATGGCA GCCTTGGTGC CATGCATGTA        480

TACGAGAGCA AGTTCCGCAA CTGGTCCGAA GGTTACTCCG ACTTCGACCG CGGAGCCTAT        540

GTGATCACCT TCATCCCCAA GAGC                                               564
```

( 2 ) INFORMATION FOR SEQ ID NO:12:

( i ) SEQUENCE CHARACTERISTICS:
        ( A ) LENGTH: 1322 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Streptoverticillium sp.

( v i i ) IMMEDIATE SOURCE:
        ( B ) CLONE: pTV118 NcoI ( x i ) SEQUENCE DESCRIPTION: SEQ ID NO:12:

```
TGCGGCGACG CGTAGGCAAT GGGGGTTCAT CGCGACGTGC TTCCGCACGG CCGCGTTCAA         60

CGATGTTCCA CGACAAAGGA GTTGCAGGTT TCC ATG CGC TAT ACG CCG GAG GCT        114
                                   Met Arg Tyr Thr Pro Glu Ala
                                   -75             -70

CTC GTC TTC GCC ACT ATG AGT GCG GTT TAT GCA CCG CCG GAT TCA TGC         162
Leu Val Phe Ala Thr Met Ser Ala Val Tyr Ala Pro Pro Asp Ser Cys
        -65             -60             -55

CGT CGG CCG GCG AGG CCG CCG CCG ACA ATG GCG CGG GGG AAG AGA CGA         210
Arg Arg Pro Ala Arg Pro Pro Pro Thr Met Ala Arg Gly Lys Arg Arg
    -50             -45             -40

AGT CCT ACG CCG AAA CCT ACC GCC TCA CGG CGG ATG ACG TCG CGA CAT         258
Ser Pro Thr Pro Lys Pro Thr Ala Ser Arg Arg Met Thr Ser Arg His
-35             -30             -25

CAA CGC GCT CAA CGA AGC GCT CCG GCC GCT TCG AGC GCC GGC CCG TCG         306
Gln Arg Ala Gln Arg Ser Ala Pro Ala Ala Ser Ser Ala Gly Pro Ser
-20             -15             -10                              -5

TTC CGG GCC CCC GAC TCC GAC GAC AGG GTC ACC CCT CCC GCC GAG CCG         354
Phe Arg Ala Pro Asp Ser Asp Asp Arg Val Thr Pro Pro Ala Glu Pro
            1               5                       10

CTC GAC AGG ATG CCC GAC CCG TAC CGT CCC TCG TAC GGC AGG GCC GAG         402
Leu Asp Arg Met Pro Asp Pro Tyr Arg Pro Ser Tyr Gly Arg Ala Glu
        15              20                      25

ACG GTC GTC AAC AAC TAC ATA CGC AAG TGG CAG CAG GTC TAC AGC CAC         450
Thr Val Val Asn Asn Tyr Ile Arg Lys Trp Gln Gln Val Tyr Ser His
    30              35                      40

CGC GAC GGC AGG AAG CAG CAG ATG ACC GAG GAG CAA CGG GAG TGG CTG         498
Arg Asp Gly Arg Lys Gln Gln Met Thr Glu Glu Gln Arg Glu Trp Leu
45              50                      55                      60

TCC TAC GGC TGC GTC GGT GTC ACC TGG GTC AAT TCG GGT CAG TAC CCC         546
Ser Tyr Gly Cys Val Gly Val Thr Trp Val Asn Ser Gly Gln Tyr Pro
                65              70                      75

ACG AAC AGA CTG GCC TTC GCG TCC TTC GAC GAG GAC AGG TTC AAG AAC         594
Thr Asn Arg Leu Ala Phe Ala Ser Phe Asp Glu Asp Arg Phe Lys Asn
            80                      85                      90

GAG CTG AAG AAC GGC AGG CCC CGG TCC GGC GAG ACG CGG GCG GAG TTC         642
Glu Leu Lys Asn Gly Arg Pro Arg Ser Gly Glu Thr Arg Ala Glu Phe
                95                      100                 105

GAG GGC CGC GTC GCG AAG GAG AGC TTT GAT GAA GAG AAG GGG TTC CAG         690
Glu Gly Arg Val Ala Lys Glu Ser Phe Asp Glu Glu Lys Gly Phe Gln
        110                     115                     120

CGG GCG CGT GAG GTG GCG TCC GTG ATG AAC AGG GCC CTG GAG AAC GCC         738
```

|  |  |  |  |  |  |  |  |  |  |  |  |  |  |  |  |
|---|---|---|---|---|---|---|---|---|---|---|---|---|---|---|---|
| Arg<br>125 | Ala | Arg | Glu | Val | Ala<br>130 | Ser | Val | Met | Asn | Arg<br>135 | Ala | Leu | Glu | Asn | Ala<br>140 |
| CAC<br>His | GAC<br>Asp | GAG<br>Glu | AGC<br>Ser | GCT<br>Ala<br>145 | TAC<br>Tyr | CTC<br>Leu | GAC<br>Asp | AAC<br>Asn | CTC<br>Leu<br>150 | AAG<br>Lys | AAG<br>Lys | GAA<br>Glu | CTG<br>Leu | GCG<br>Ala<br>155 | AAC<br>Asn | 786 |
| GGC<br>Gly | AAC<br>Asn | GAC<br>Asp | GCC<br>Ala<br>160 | CTG<br>Leu | CGC<br>Arg | AAC<br>Asn | GAG<br>Glu | GAC<br>Asp<br>165 | GCC<br>Ala | CGT<br>Arg | TCC<br>Ser | CCG<br>Pro | TTC<br>Phe<br>170 | TAC<br>Tyr | TCG<br>Ser | 834 |
| GCG<br>Ala | CTG<br>Leu | CGG<br>Arg<br>175 | AAC<br>Asn | ACG<br>Thr | CCG<br>Pro | TCC<br>Ser | TTT<br>Phe<br>180 | AAG<br>Lys | GAG<br>Glu | CGG<br>Arg | AAC<br>Asn | GGA<br>Gly<br>185 | GGC<br>Gly | AAT<br>Asn | CAC<br>His | 882 |
| GAC<br>Asp | CCG<br>Pro<br>190 | TCC<br>Ser | AGG<br>Arg | ATG<br>Met | AAG<br>Lys | GCC<br>Ala<br>195 | GTC<br>Val | ATC<br>Ile | TAC<br>Tyr | TCG<br>Ser | AAG<br>Lys<br>200 | CAC<br>His | TTC<br>Phe | TGG<br>Trp | AGC<br>Ser | 930 |
| GGC<br>Gly<br>205 | CAG<br>Gln | GAC<br>Asp | CGG<br>Arg | TCG<br>Ser | AGT<br>Ser<br>210 | TCG<br>Ser | GCC<br>Ala | GAC<br>Asp | AAG<br>Lys | AGG<br>Arg<br>215 | AAG<br>Lys | TAC<br>Tyr | GGC<br>Gly | GAC<br>Asp | CCG<br>Pro<br>220 | 978 |
| GAC<br>Asp | GCT<br>Ala | TTC<br>Phe | CGC<br>Arg<br>225 | CCG<br>Pro | GCC<br>Ala | CCC<br>Pro | GGG<br>Gly | ACC<br>Thr<br>230 | GGC<br>Gly | CTG<br>Leu | GTC<br>Val | GAC<br>Asp | ATG<br>Met<br>235 | TCG<br>Ser | AGG<br>Arg | 1026 |
| GAC<br>Asp | AGG<br>Arg | AAC<br>Asn | ATT<br>Ile<br>240 | CCG<br>Pro | CGC<br>Arg | AGC<br>Ser | CCC<br>Pro | ACC<br>Thr<br>245 | AGC<br>Ser | CCC<br>Pro | GGT<br>Gly | GAG<br>Glu | GGA<br>Gly<br>250 | TTC<br>Phe | GTC<br>Val | 1074 |
| AAT<br>Asn | TTC<br>Phe | GAC<br>Asp | TAC<br>Tyr<br>255 | GGC<br>Gly | TGG<br>Trp | TTC<br>Phe | GGC<br>Gly | GCC<br>Ala<br>260 | CAG<br>Gln | ACG<br>Thr | GAA<br>Glu | GCG<br>Ala | GAC<br>Asp<br>265 | GCC<br>Ala | GAC<br>Asp | 1122 |
| AAG<br>Lys | ACC<br>Thr<br>270 | GTC<br>Val | TGG<br>Trp | ACC<br>Thr | CAC<br>His | GGA<br>Gly<br>275 | AAT<br>Asn | CAC<br>His | TAT<br>Tyr | CAC<br>His | GCG<br>Ala<br>280 | CCC<br>Pro | AAT<br>Asn | GGC<br>Gly | AGC<br>Ser | 1170 |
| CTT<br>Leu<br>285 | GGT<br>Gly | GCC<br>Ala | ATG<br>Met | CAT<br>His | GTA<br>Val<br>290 | TAC<br>Tyr | GAG<br>Glu | AGC<br>Ser | AAG<br>Lys | TTC<br>Phe<br>295 | CGC<br>Arg | AAC<br>Asn | TGG<br>Trp | TCC<br>Ser | GAA<br>Glu<br>300 | 1218 |
| GGT<br>Gly | TAC<br>Tyr | TCC<br>Ser | GAC<br>Asp | TTC<br>Phe<br>305 | GAC<br>Asp | CGC<br>Arg | GGA<br>Gly | GCC<br>Ala | TAT<br>Tyr<br>310 | GTG<br>Val | ATC<br>Ile | ACC<br>Thr | TTC<br>Phe | ATC<br>Ile<br>315 | CCC<br>Pro | 1266 |
| AAG<br>Lys | AGC<br>Ser | TGG<br>Trp | AAC<br>Asn<br>320 | ACC<br>Thr | GCC<br>Ala | CCC<br>Pro | GAC<br>Asp | AAG<br>Lys<br>325 | GTA<br>Val | AAG<br>Lys | CAG<br>Gln | GGC<br>Gly | TGG<br>Trp<br>330 | CCG<br>Pro |  | 1311 |

TGATGTGAGC G                                                                                                                                                                                                                                                                                                                                                                                                      1322

( 2 ) INFORMATION FOR SEQ ID NO:13:

( i ) SEQUENCE CHARACTERISTICS:
        ( A ) LENGTH: 406 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Met<br>-75 | Arg | Tyr | Thr | Pro | Glu<br>-70 | Ala | Leu | Val | Phe | Ala<br>-65 | Thr | Met | Ser | Ala | Val<br>-60 |
|---|---|---|---|---|---|---|---|---|---|---|---|---|---|---|---|
| Tyr | Ala | Pro | Pro | Asp<br>-55 | Ser | Cys | Arg | Arg | Pro<br>-50 | Ala | Arg | Pro | Pro<br>-45 | Thr |  |
| Met | Ala | Arg | Gly<br>-40 | Lys | Arg | Arg | Ser | Pro<br>-35 | Thr | Pro | Lys | Pro | Thr<br>-30 | Ala | Ser |
| Arg | Arg | Met<br>-25 | Thr | Ser | Arg | His | Gln<br>-20 | Arg | Ala | Gln | Arg | Ser<br>-15 | Ala | Pro | Ala |
| Ala | Ser<br>-10 | Ser | Ala | Gly | Pro | Ser<br>-5 | Phe | Arg | Ala | Pro | Asp | Ser<br>1 | Asp | Asp | Arg<br>5 |
| Val | Thr | Pro | Pro | Ala<br>10 | Glu | Pro | Leu | Asp | Arg<br>15 | Met | Pro | Asp | Pro | Tyr<br>20 | Arg |

```
Pro  Ser  Tyr  Gly  Arg  Ala  Glu  Thr  Val  Val  Asn  Asn  Tyr  Ile  Arg  Lys
              25                      30                      35

Trp  Gln  Gln  Val  Tyr  Ser  His  Arg  Asp  Gly  Arg  Lys  Gln  Gln  Met  Thr
         40                       45                      50

Glu  Glu  Gln  Arg  Glu  Trp  Leu  Ser  Tyr  Gly  Cys  Val  Gly  Val  Thr  Trp
     55                       60                      65

Val  Asn  Ser  Gly  Gln  Tyr  Pro  Thr  Asn  Arg  Leu  Ala  Phe  Ala  Ser  Phe
70                       75                      80                           85

Asp  Glu  Asp  Arg  Phe  Lys  Asn  Glu  Leu  Lys  Asn  Gly  Arg  Pro  Arg  Ser
                    90                      95                      100

Gly  Glu  Thr  Arg  Ala  Glu  Phe  Glu  Gly  Arg  Val  Ala  Lys  Glu  Ser  Phe
               105                      110                     115

Asp  Glu  Glu  Lys  Gly  Phe  Gln  Arg  Ala  Arg  Glu  Val  Ala  Ser  Val  Met
               120                      125                     130

Asn  Arg  Ala  Leu  Glu  Asn  Ala  His  Asp  Glu  Ser  Ala  Tyr  Leu  Asp  Asn
         135                      140                     145

Leu  Lys  Lys  Glu  Leu  Ala  Asn  Gly  Asn  Asp  Ala  Leu  Arg  Asn  Glu  Asp
150                      155                      160                          165

Ala  Arg  Ser  Pro  Phe  Tyr  Ser  Ala  Leu  Arg  Asn  Thr  Pro  Ser  Phe  Lys
                    170                      175                     180

Glu  Arg  Asn  Gly  Gly  Asn  His  Asp  Pro  Ser  Arg  Met  Lys  Ala  Val  Ile
               185                      190                     195

Tyr  Ser  Lys  His  Phe  Trp  Ser  Gly  Gln  Asp  Arg  Ser  Ser  Ser  Ala  Asp
               200                      205                     210

Lys  Arg  Lys  Tyr  Gly  Asp  Pro  Asp  Ala  Phe  Arg  Pro  Ala  Pro  Gly  Thr
     215                      220                      225

Gly  Leu  Val  Asp  Met  Ser  Arg  Asp  Arg  Asn  Ile  Pro  Arg  Ser  Pro  Thr
230                      235                      240                          245

Ser  Pro  Gly  Glu  Gly  Phe  Val  Asn  Phe  Asp  Tyr  Gly  Trp  Phe  Gly  Ala
               250                      255                     260

Gln  Thr  Glu  Ala  Asp  Ala  Asp  Lys  Thr  Val  Trp  Thr  His  Gly  Asn  His
               265                      270                     275

Tyr  His  Ala  Pro  Asn  Gly  Ser  Leu  Gly  Ala  Met  His  Val  Tyr  Glu  Ser
               280                      285                     290

Lys  Phe  Arg  Asn  Trp  Ser  Glu  Gly  Tyr  Ser  Asp  Phe  Asp  Arg  Gly  Ala
     295                      300                      305

Tyr  Val  Ile  Thr  Phe  Ile  Pro  Lys  Ser  Trp  Asn  Thr  Ala  Pro  Asp  Lys
310                      315                      320                          325

Val  Lys  Gln  Gly  Trp  Pro
               330
```

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:14:

ACGAGCTCAA AGGAGTTGCA GGTTTCCATG CGCTAT        36

( 2 ) INFORMATION FOR SEQ ID NO:15:

( i ) SEQUENCE CHARACTERISTICS:
        ( A ) LENGTH: 36 base pairs
        ( B ) TYPE: nucleic acid ( C ) STRANDEDNESS: single
( D ) TOPOLOGY: linear ( i i ) MOLECULE TYPE: Other nucleic acid (synthetic DNA)

( x i ) SEQUENCE DESCRIPTION: SEQ ID NO:15:

CCGGATCCAG ATCTCACATC ACGGCCAGCC CTGCTT 36

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:16:

ACGAGCTCGT TGGGTTGACG ACCCCG 26

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO:17:

ACGAATTCTG CAGTTTTCGC ACGTGAGCCA 30

( 2 ) INFORMATION FOR SEQ ID NO:18:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( x i ) SEQUENCE DESCRIPTION: SEQ ID NO:18:

AGCTTGGGAT TCTGATGACA GAGTCACTCC ACCAG 35

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( x i ) SEQUENCE DESCRIPTION: SEQ ID NO:19:

CTGGTGGAGT GACTCTGTCA TCAGAATCCC A 31

( 2 ) INFORMATION FOR SEQ ID NO:20:

( i ) SEQUENCE CHARACTERISTICS:
        ( A ) LENGTH: 152 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( x i ) SEQUENCE DESCRIPTION: SEQ ID NO:20:

```
AGCTTGG AAG AGA AGA TCT CCA ACT CCA AAG CCA ACT GCT TCT AGA AGA         49
        Lys Arg Arg Ser Pro Thr Pro Lys Pro Thr Ala Ser Arg Arg
        -39             -35             -30

ATG ACT TCT AGA CAC CAA AGA GCT CAA AGA TCT GCT CCA GCT GCT TCT         97
Met Thr Ser Arg His Gln Arg Ala Gln Arg Ser Ala Pro Ala Ala Ser
-25             -20             -15                         -10

TCT GCT GGT CCA TCT TTC AGA GCT CCA GAT TCT GAT GAC AGA GTC ACT         145
Ser Ala Gly Pro Ser Phe Arg Ala Pro Asp Ser Asp Asp Arg Val Thr
                -5                   1               5

CCA CCA G                                                                152
Pro Pro
```

( 2 ) INFORMATION FOR SEQ ID NO:21:

( i ) SEQUENCE CHARACTERISTICS:
        ( A ) LENGTH: 48 amino acids
        ( B ) TYPE: amino acid
        ( D ) TOPOLOGY: linear ( x i ) SEQUENCE DESCRIPTION: SEQ ID NO:21:

```
Lys Arg Arg Ser Pro Thr Pro Lys Pro Thr Ala Ser Arg Arg Met Thr
-39             -35             -30                         -25

Ser Arg His Gln Arg Ala Gln Arg Ser Ala Pro Ala Ala Ser Ser Ala
            -20             -15                         -10

Gly Pro Ser Phe Arg Ala Pro Asp Ser Asp Asp Arg Val Thr Pro Pro
        -5                   1               5
```

( 2 ) INFORMATION FOR SEQ ID NO:22:

( i ) SEQUENCE CHARACTERISTICS:
        ( A ) LENGTH: 148 base pairs
        ( B ) TYPE: nucleic acid
        ( C ) STRANDEDNESS: double
        ( D ) TOPOLOGY: linear ( i i ) MOLECULE TYPE: Other nucleic acid (synthetic DNA)

( x i ) SEQUENCE DESCRIPTION: SEQ ID NO:22:

```
CTGGTGGAGT GACTCTGTCA TCAGAATCTG GAGCTCTGAA AGATGGACCA GCAGAAGAAG    60

CAGCTGGAGC AGATCTTTGA GCTCTTTGGT GTCTAGAAGT CATTCTTCTA GAAGCAGTTG    120

GCTTTGGAGT TGGAGATCTT CTCTTCCA                                       148
```

RECOMBINANT TRANSGLUTAMINASE

This is a continuation of application Ser. No. 07/777,447, filed Oct. 18, 1991, now abandoned.

FIELD OF THE INVENTION

This invention relates to a DNA gene which encodes transglutaminase, a plasmid in which the gene is incorporated, a transformant transformed with the plasmid and a process for the production of transglutaminase which comprises culturing the transformant.

BACKGROUND OF THE INVENTION

Transglutaminase (hereinafter, referred to as "BTG") is an enzyme which catalyzes an acyl transfer reaction of a γ-carboxyamide group of glutamine residue in a peptide chain.

BTG induces intramolecular or intermolecular formation of ε-(γ-Gln)-Lys cross linking when an ε-amino group of a lysine residue in a protein molecule functions as an acyl receptor. Also, when water functions as an acyl receptor, this enzyme accelerates conversion of glutamine residues into glutamic acid residues by deamidation.

Because of its function to gel protein, BTG has been employed in the production of gelled food, gelled cosmetics, yogurt, gelatins, cheese and the like (JP-B-1-50382). (The term "JP-B" as used herein means an "examined Japanese patent publication".) This enzyme has also been employed in the production of thermally stable materials such as microcapsules, carriers of immobilized enzymes and the like.

BTG has been found in animals, for example, in the liver of guinea pigs (Connellan et al., *Journal of Biological Chemistry*, vol. 246, No. 4, pp. 1093–1098 (1971)) and in various organs and blood of mammals (Folk et al., *Advances in Enzymology*, vol. 38, pp. 109–191 (1973); and Folk et al., *Advances in Protein Chemistry*, vol. 31, pp. 1–133 (1977)), and its enzymological properties have been studied. In addition, a different type of BTG, which is independent of calcium ($Ca^{2+}$) and is therefore different from the animal-derived BTG, has been found in various strains of the genus Streptoverticillium. Illustrative examples of these strains include *Streptoverticillium griseocarneum* IFO 12776, *Streptoverticillium cinnamoneum* sub sp. cinnamoneum IFO 12852, *Streptoverticillium mobaraense* IFO 13819 and other species (cf. JP-A-64-27471). (The term "JP-A" as used herein means an "unexamined published Japanese patent application".)

Since BTG is obtained from animals, micro-organisms and the like, there are many problems to be solved such as a low production yield and an expensive production cost.

As a result of extensive investigations to overcome these problems of the prior art, the inventors of the present invention have succeeded in isolating and purifying a DNA gene which encodes BTG and determining its base sequence. On the basis of these results, the present inventors have provided a method for producing BTG efficiently in a large quantity through expression of the DNA gene in microorganisms such as *Escherichia coli* using genetic engineering.

SUMMARY OF THE INVENTION

In view of the above, it therefore is a primary object of the present invention to provide a DNA fragment which encodes transglutaminase, a plasmid in which the DNA fragment is incorporated, a transformant transformed with the plasmid and a process for the production of transglutaminase that comprises culturing the transformant.

These and other objects and advantages of the present invention will become apparent from the following description.

BRIEF DESCRIPTION OF THE ACCOMPANYING DRAWING

The drawing shows the results of Western blotting obtained in Example 4 hereinafter.

DETAILED DESCRIPTION OF THE INVENTION

In accordance with the present invention, there is provided a DNA fragment which encodes BTG, more particularly, a DNA fragment containing a base sequence that encodes an amino acid sequence as shown in the Table 1 below wherein each amino acid is indicated by the corresponding single letter code.

TABLE 1

| 10 | 20 | 30 | 40 |
|---|---|---|---|
| D S D D R V T P P A | E P L D R M P D P Y | R S P Y G R A E T V | V N N Y I R K W Q Q |
| 50 | 60 | 70 | 80 |
| V Y S H R D G R K Q | Q M T E E Q R E W L | S Y G C V G V T W V | N S G Q Y P T N R L |
| 90 | 100 | 110 | 120 |
| A F A S F D E D R F | K N E L K N G R P R | S G E T R A E F E G | R V A K E S F D E E |
| 130 | 140 | 150 | 160 |
| K G F Q R A R E V A | S V N M R A L E N A | H D E S A Y L D N L | K K E L A N G N D A |
| 170 | 180 | 190 | 200 |
| L R N E D A R S P F | Y S A L R N T P S F | K E R N G G N H D P | S R M K A V I Y S K |
| 210 | 220 | 230 | 240 |
| H F W S G Q D R S S | S A D K R K Y G D P | D A F R P A P G T G | L V D M S R D R N I |
| 250 | 260 | 270 | 280 |
| P R S P T S P G E G | F V N F D Y G W F G | A Q T E A D A D K T | V W T H G N H Y H A |
| 290 | 300 | 310 | 320 |
| P N G S L G A M H V | Y E S K F R N W S E | G Y S D F D R G A Y | V I T F I P K S W N |
| 330 | | | |
| T A P D K V K Q G W | P | | |

TABLE 1-continued (SEQ ID NO: 1)

This DNA fragment can include various alternative base sequences when codon degeneracy is taken into consideration and these are within the scope of the present invention. It is apparent that these base sequences can be selected easily by those skilled in the art based on many factors related to the genetic expression system such as host cell-dependent preferential codons and the like.

As an illustrative example of such a case, a base sequence which can be used suitably in an expression system using *E. coli* or yeast as the host cell is shown in Table 2 below.

The DNA fragment shown in Table 1 above can be easily prepared by prior art techniques such as chemical synthesis and the like, for example, the phosphormidite method (M. H. Caruthers, *Science,* 230, 281 (1985) and Sinha, N. D. et al., *Nucleic Acids Res.,* 12, 4539–4557 (1984).

A further illustrative example of a DNA fragment containing a base sequence coding for the amino acid sequence shown in Table 1 is the structural gene of BTG corresponding to the amino acid sequence shown in Table 1, which is shown in Table 3 below.

TABLE 2

| | | | | | | | | | |
|---|---|---|---|---|---|---|---|---|---|
| GAT | TCT | GAT | GAC | AGA | GTC | ACT | CCA | CCA | GCT |
| GAA | CCA | TTG | GAT | AGA | ATG | CCA | GAT | CCA | TAC |
| AGA | CCA | TCT | TAC | GGT | AGA | GCT | GAA | ACT | GTT |
| GTC | AAC | AAC | TAC | ATT | AGA | AAG | TGG | CAA | CAA |
| GTC | TAC | TCT | CAC | AGA | GAT | GGT | AGA | AAG | CAA |
| CAA | ATG | ACT | GAA | GAA | CAA | AGA | GAA | TGG | TTG |
| TCT | TAC | GGT | TGT | GTT | GGT | GTT | ACT | TGG | GTT |
| AAC | TCT | GGT | CAA | TAC | CCA | ACT | AAC | AGA | TTG |
| GCT | TTC | GCT | TCT | TTC | GAT | GAA | GAT | AGA | TTC |
| AAG | AAC | GAA | TTG | AAG | AAC | GGT | AGA | CCA | AGA |
| TCC | GGT | GAA | ACT | AGA | GCT | GAA | TTC | GAA | GGT |
| AGA | GTT | GCT | AAG | GAA | TCT | TTC | GAT | GAA | GAA |
| AAG | GGT | TTC | CAA | AGA | GCT | AGA | GAA | GTT | GCT |
| TCT | GTT | ATG | AAC | AGA | GCT | CTA | GAA | AAC | GCT |
| CAC | GAT | GAA | TCT | GCT | TAC | TTG | GAT | AAC | TTG |
| AAG | AAG | GAA | TTG | GCC | AAC | GGT | AAC | GAT | GCT |
| TTG | AGA | AAC | GAA | GAT | GCT | AGA | TCC | CCA | TTC |
| TAC | TCT | GCT | TTG | AGA | AAC | ACT | CCA | TCT | TTC |
| AAG | GAA | AGA | AAC | GGT | GGT | AAC | CAC | GAT | CCA |
| TCC | AGA | ATG | AAG | GCT | GTT | ATT | TAC | TCT | AAG |
| CAC | TTC | TGG | TCT | GGT | CAA | GAT | AGA | TCT | TCT |
| TCT | GCT | GAT | AAG | AGA | AAG | TAC | GGT | GAT | CCA |
| GAT | GCT | TTC | AGA | CCA | GCT | CCA | GGT | ACC | GGT |
| TTG | GTC | GAC | ATG | TCC | AGA | GAT | AGA | AAC | ATT |
| CCA | AGA | TCC | CCA | ACT | TCT | CCA | GGT | GAA | GGT |
| TTC | GTC | AAC | TTC | GAT | TAC | GGT | TGG | TTC | GGT |
| GCT | CAA | ACT | GAA | GCT | GAT | GCT | GAT | AAG | ACT |
| GTT | TGG | ACC | CAT | GGT | AAC | CAC | TAC | CAC | GCT |
| CCA | AAC | GGT | TCT | TTG | GGT | GCT | ATG | CAC | GTC |
| TAC | GAA | TCT | AAG | TTC | AGA | AAC | TGG | TCT | GAA |
| GGT | TAC | TCT | GAT | TTC | GAT | AGA | GGT | GCT | TAC |
| GTT | ATT | ACT | TTC | ATT | CCA | AAG | TCT | TGG | AAC |
| ACT | GCT | CCA | GAC | AAG | GTC | AAG | CAA | GGT | TGG |
| CCA | | | | | | | | | |
| (SEQ ID NO: 2) | | | | | | | | | |

TABLE 3

GACTCCGACGACAGGGTCACCCCTCCCGCCGAGCCGCTCGACAGGATGCCCGACCC

GTACCGTCCCTCGTACGGCAGGGCCGAGACGGTCGTCAACAACTACATACGCAAGT

GGCAGCAGGTCTACAGCCACCGCGACGGCAGGAAGCAGCAGATGACCGAGGAGCAA

CGGGAGTGGCTGTCCTACGGCTGCGTCGGTGTCACCTGGGTCAATTCGGGTCAGTA

CCCCACGAACAGACTGGCCTTCGCGTCCTTCGACGAGGACAGGTTCAAGAACGAGC

TGAAGAACGGCAGGCCCCGGTCCGGCGAGACGCGGGCGGAGTTCGAGGGCGCGCTC

GCGAAGGAGAGCTTTGATGAAGAGAAGGGGTTCCAGCGGGCGCGTGAGGTGGCGTC

CGTGATGAACAGGGCCCTGGAGAACGCCCACGACGAGAGCGCTTACCTCGACAACC

TCAAGAAGGAACTGGCGAACGGCAACGACGCCCTGCGCAACGAGGACGCCCGTTCC

CCGTTCTACTCGGCGCTGCGGAACACGCCGTCCTTTAAGGAGCGGAACGGAGGCAA

TCACGACCCGTCCAGGATGAAGGCCGTCATCTACTCGAAGCACTTCTGGAGCGGCC

TABLE 3-continued

AGGACCGGTCGAGTTCGGCCGACAAGAGGAAGTACGGCGACCCGGACGCTTTCCGC

CCGGCCCCGGGACCGGCCTGGTCGACATGTCGAGGGACAGGAACATTCCGCGCAG

CCCCACCAGCCCCGGTGAGGGATTCGTCAATTTCGACTACGGCTGGTTCGGCGCCC

AGACGGAAGCGGACGCCGACAAGACCGTCTGGACCCACGGAAATCACTATCACGCG

CCCAATGGCAGCCTTGGTGCCATGCATGTATACGAGAGCAAGTTCCGCAACTGGTC

CGAAGGTTACTCCGACTTCGACCGCGGAGCCTATGTGATCACCTTCATCCCCAAGA

GCTGGAACACCGCCCCCGACAAGGTAAAGCAGGGCTGGCCG (SEQ ID NO: 3)

The DNA fragment according to the present invention is not particularly limited to the DNA fragment containing a base sequence that encodes the amino acid sequence shown in Table 1. The encoded amino acid sequence may be different from the sequence shown in Table 1 in that a part of the sequence thereof is missing or replaced with some other amino acid sequence and/or in that some other amino acid sequence is added to or inserted in the sequence, provided that a protein having such an amino acid sequence has transglutaminase activity or can be processed to become a mature protein which has transglutaminase activity. Thus, a DNA fragment containing a base sequence coding for such a different amino acid sequence is also included within the scope of the present invention.

The present invention also provides a DNA fragment containing a base sequence coding for an amino acid sequence in which 5′ end of the DNA sequence encoding the amino acid sequence of Table 1 is further connected with a DNA fragment encoding all or part of the amino acid sequence containing a signal peptide as shown in Table 4 below.

TABLE 4

| −75 | −70 | −60 | −50 |
|---|---|---|---|
| MRYTP | EALVFATMSA | VYAPPDSCRR | PARPPPTMAR |

| −40 | −30 | −20 | −10 |
|---|---|---|---|
| GKRRSPTPKP | TASRRMTSRH | QRAQRSAPAA | SSAGPSFRAP |

(SEQ ID NO: 4)

An example of the part of the amino acid sequence shown in Table 4 is shown in Table 5 below.

TABLE 5

| −39 | −30 | −20 | −10 |
|---|---|---|---|
| KRRSPTPKP | TASRRMTSRH | QRAQRSAPAA | SSAGPSFRAP |

(SEQ ID NO: 5)

The above-described DNA fragments can also include various base sequences based on codon degeneracy, and they can be prepared by various well known techniques including chemical synthesis.

An example of a base sequence of a DNA fragment encoding the amino acid sequence containing a signal peptide as shown in Table 4 is shown in Table 6 below.

TABLE 6

ATGCGCTATACGCCGGAGGCTCTCGTCTTCGCCACTATGAGTGCGGTTTATGCACC

GCCGGATTCATGCCGTCGGCCGGCGAGGCCGCCGCCGACAATGGCGCGGGGGAAGA

GACGAAGTCCTACGCCGAAACCTACCGCCTCACGGCGGATGACGTCGCGACATCAA

CGCGCTCAACGAAGCGCTCCGGCCGCTTCGAGCGCCGGCCCGTCGTTCCGGGCCCC

C (SEQ ID NO: 6)

An example of a base sequence of a DNA fragment encoding the amino acid sequence as shown in Table 5 is shown in Table 7 below.

TABLE 7

AAGAGAAGATCTCCAACTCCAAAGCCAACTGCTTCTAGAAGAATGACTTCTAGACA

CCAAAGAGCTCAAAGATCTGCTCCAGCTGCTTCTTCTGCTGGTCCATCTTTCAGAG

CTCCA (SEQ ID NO: 7)

The DNA fragment according to the present invention can be also produced by cloning it from genomic DNA library of actinomycetes using a DNA fragment as a probe prepared using polymerase chain reaction (PCR) technology (R. F. Saiki et al., *Science*, 239, 487 (1988) and K. B. Mullis and F. A. Faloona, *Methods Enzymol.*, 155, 335 (1989)). An example of a base sequence of a DNA fragment obtained in this manner which contains all of the above-described DNA fragment, i.e., the structural gene of BTG and an upstream portion from its 5′ end is shown in Table 8 below.

TABLE 8

```
ATGCGCTATACGCCGGAGGCTCTCGTCTTCGCCACTATGAGTGCGGTTTATGCACC
GCCGGATTCATGCCGTCGGCCGGCGAGGCCGCCGCCGACAATGGCGCGGGGGAAGA
GACGAAGTCCTACGCCGAAACCTACCGCCTCACGGCGGATGACGTCGCGACATCAA
CGCGCTCAACGAAGCGCTCCGGCCGCTTCGAGCGCCGGCCCGTCGTTCCGGGCCCC
CGACTCCGACGACAGGGTCACCCCTCCCGCCGAGCCGCTCGACAGGATGCCCGACC
CGTACCGTCCCTCGTACGGCAGGGCCGAGACGGTCGTCAACAACTACATACGCAAG
TGGCAGCAGGTCTACAGCCACCGCGACGGCAGGAAGCAGCAGATGACCGAGGAGCA
ACGGGAGTGGCTGTCCTACGGCTGCGTCGGTGTCACCTGGGTCAATTCGGGTCAGT
ACCCCACGAACAGACTGGCCTTCGCGTCCTTCGACGAGGACAGGTTCAAGAACGAG
CTGAAGAACGGCAGGCCCCGGTCCGGCGAGACGCGGGCGGAGTTCGAGGGCCGCGT
CGCGAAGGAGAGCTTTGATGAAGAGAAGGGGTTCCAGCGGGCGCGTGAGGTGGCGT
CCGTGATGAACAGGGCCCTGGAGAACGCCCACGACGAGAGCGCTTACCTCGACAAC
CTCAAGAAGGAACTGGCGAACGGCAACGACGCCCTGCGCAACGAGGACGCCCGTTC
CCCGTTCTACTCGGCGCTGCGGAACACGCCGTCCTTTAAGGAGCGGAACGGAGGCA
ATCACGACCCGTCCAGGATGAAGGCCGTCATCTACTCGAAGCACTTCTGGAGCGGC
CAGGACCGGTCGAGTTCGGCCGACAAGAGGAAGTACGGCGACCCGGACGCTTTCCG
CCCGGCCCCCGGGACCGGCCTGGTCGACATGTCGAGGGACAGGAACATTCCGCGCA
GCCCCACCAGCCCCGGTGAGGGATTCGTCAATTTCGACTACGGCTGGTTCGGCGCC
CAGACGGAAGCGGACGCCGACAAGACCGTCTGGACCCACGGAAATCACTATCACGC
GCCCAATGGCAGCCTTGGTGCCATGCATGTATACGAGAGCAAGTTCCGCAACTGGT
CCGAAGGTTACTCCGACTTCGACCGCGGAGCCTATGTGATCACCTTCATCCCCAAG
AGCTGGAACACCGCCCCCGACAAGGTAAAGCAGGGCTGGCCG
```

(SEQ ID NO: 8)

According to the present invention, there is also provided a vector which can be used for expression and secretion of BTG.

Such a vector may be prepared using conventional techniques by inserting a DNA fragment containing a base sequence which encodes the amino acid sequence shown in Table 1 into a known expression vector which is selected depending on the expression system desired. For example, when an *E. coli* strain is used as the host cell, commonly used vectors such as pTrc99A (Pharmacia); pPROK-C and pKK233-2 (Clontech Co.); and pNH8a, pNH16a, pNH18a, pcDNAII, and pAX (Stratagene) can be used for the construction of an expression secretion vector of the present invention. In addition, a plasmid pIN-III-ompA2 can be also used preferably. A plasmid, designated herein pOMPA-BTG, is an illustrative example of the expression secretion plasmid of the present invention which has been constructed by inserting the DNA fragment of the present invention into pIN-III-ompA2.

When an actinomycetes strain is used as the host cell, commonly used vectors such as pIJ 41, pSEV 2, pOA 154 and pSCP 111, etc. can be also used. In addition, pIJ 702 can be also used preferably. Further, when a yeast strain is used as the host cell, commonly used vectors such as pAM82, pYG100, YEp52, pAAH5, YCpAD1, pYαEGF-23, YEpIPT-ISIFN-α2, CPOTinsulin and pcD-Y (cf. *Jikkenigaku*, vol. 5, No. 11, 138 (1987)), etc. can be used. In addition, an *E. Coli*-yeast shuttle vector pNJ 1053 can be also used preferably. Illustrative examples of the expression secretion vector of the present invention which has been constructed by inserting the DNA fragment of the present invention into these vectors are pIJ702-BTG, pNJ1053-proBTG, and pNJ1053-BTG.

The present invention also relates to various transformants obtained by transforming host cells with the BTG gene-carrying expression and secretion vector.

Host cells suitable for use in such transformation purpose may be selected from various procaryotic cells and eucaryotic cells. As the procaryotic host, *E. coli* strains, Bacillus strains such as *B. subtilis*, actinomycetes (particularly, Streptomyces strains such as *Streptomyces lividans, Streptomyces coelicolor, Streptomyces kasugaensis,* and *Streptomyces parvulus*), and the like may be mentioned. As the eucaryotic host, yeasts (particularly, Saccharomyces strains such as *Saccharomyces cerevisiae*), other fungi such as Aspergillus strains etc., and the like may be mentioned.

An illustrative example of a useful *E. coli* strain is JA 221 strain (hsdM+, trpE5, leuB6, lacY, recA/F', lacIq, lac+, pro+). A transformant was obtained by transforming *E. coli* JA 221 strain with the inventive expression and secretion plasmid pOMPA-BTG. This transformant, designated AJ12569 herein, was deposited by the present inventors on Sep. 28, 1990, with Fermentation Research Institute, Agency of Industrial Science and Technology under the deposit number FERM P-11745 (FERM BP-3558 under the Budapest Treaty).

An illustrative example of a useful actinomycetes strain is *Streptomyces lividans* 3131-TS which was isolated from *Streptomyces lividans* 3131 as an thio-strepton-sensitive strain. A transformant which was obtained by transforming *Streptomyces lividans* 3131-TS with the inventive expression and secretion vector pIJ702-BTG, described *Streptomyces lividans* AKW-1, was deposited by the present inventors on Sep. 30, 1991, with Fermentation Research Institute, Agency of Industrial Science and Technology under the deposit number FERM BP-3586 under the Budapest Treaty.

An illustrative example of a useful yeast strain is *Saccharomyces cerevisiae* KSC22-IC (MATa, ssl 1, leu 2, his−, ura 3). A transformant which was obtained by transforming *Saccharomyces cerevisiae* KSC22-IC with the inventive expression and secretion vector pNJ1053-proBTG, designated *Saccharomyces cerevisiae* AJ 14669, was deposited by the present inventors on Sep. 30, 1991, with Fermentation Research Institute, Agency of Industrial Science and Technology under the deposit number FERM BP-3585 under the Budapest Treaty.

The present invention also provides a process for the production of a protein having BTG activity which comprises culturing the above transformant.

The culturing conditions are not strictly limited and therefore can be suitably designed by those skilled in the art depending on the type of transformant to be desired.

For example, M9 $CA_{50}$ medium and M9 medium shown below can be used preferably for culturing *E. Coli* transformant.

| M9 $CA_{50}$ | | M9 | |
|---|---|---|---|
| Casamino acid | 2% | $Na_2HPO_4$ | 0.6% |
| Glucose | 0.4% | $KH_2PO_4$ | 0.3% |
| 0.8 mM $MgSO_4$ | | NaCl | 0.05% |
| L-Tryptophan | 50 μg/ml | $NH_4Cl$ | 0.1% |
| Thiamine-HCl | 0.5 μg/ml | | |
| Ampicilline | 50 μg/ml | | |

If necessary, expression of a gene of interest may be induced by adding an expression inducer such as IPTG (isopropyl-β-D-thiogalactopyranoside) to the culture medium used.

The thus expressed protein may be isolated and purified from culture filtrate, periplasm or cytoplasm of the host cells using various prior art means (cf. *Protein Purification—Principles and Practice*, Robert K. Scopes, Springer-Verlag, New York (1982); D. Koshland and D. Bostein, *Cell*, 20, 749 (1980); and R. A. Hitzeman et al., *Science*, 219, 620 (1983), etc.).

Examples of the present invention are given below by way of illustration but are not to be construed as limiting the present invention. Unless otherwise indicated, all parts, percents, ratios and the like are by weight.

EXAMPLE 1

Cloning of BTG gene (1) Preparation of Cells

An actinomycete, Streptoverticillium sp. was cultured at 30° C. for 5 days in the following medium.

| GP Medium | |
|---|---|
| Glycerol | 0.4 wt % |
| Peptone | 0.1 wt % |
| Yeast Extracts | 0.4 wt % |
| $MgSO_4$ | 0.05 wt % |
| $KH_2PO_4$ | 0.2 wt % |
| $Na_2HPO_4$ | 0.5 wt % |
| Glycine | 0.1 wt %/1 liter |

(2) Preparation of DNA from Cells

A 400 ml portion of the cultured broth obtained above was centrifuged at 12,000×g and at 4° C. for 10 minutes, and the resulting pellet (cells) was suspended in a solution consisting of 50 mM Tris-HCl (pH 8.0), 5 mM EDTA and 50 mM NaCl (hereinafter, referred to as "TES"). The cell suspension thus prepared was centrifuged at 1,100×g at room temperature for 10 minutes, and the resulting pellet (cells) was suspended in 5 ml of TES which had been supplemented with 2 mg/ml of lysozyme (Sigma Chemical Co.). After incubating the cell suspension at 37° C. for 1 hour, the resulting lysate was frozen rapidly in acetone-dry ice and then suspended thoroughly in 42 ml of a solution consisting of 100 mM Tris-HCl (pH 9.0), 1% SDS and 100 mM NaCl (hereinafter, referred to as "Tris-SDS"). The resulting suspension was incubated at 60° C. for 20 minutes, followed by immediate freezing in acetone-dry ice for 10 minutes. After re-incubation at 60° C., the resulting sample was extracted twice with phenol which has been saturated with Tris-SDS. Thereafter, two volumes of ethanol was added to the extract thus obtained, and filaments of DNA molecules formed in the mixture solution were recovered by winding them around a glass rod. DNA molecules thus recovered were washed with 80% ethanol, dried in a desiccator equipped with an aspirator and then dissolved in 5 ml of a solution consisting of 10 mM Tris-HCl (pH 8.0) and 1 mM EDTA (hereinafter, referred to as "TE").

Next, RNA in the thus prepared DNA sample was digested and removed. For this purpose, the DNA sample was dissolved in 5 ml of TE and was mixed with 0.5 ml of a solution consisting of 1 mg/ml of RNase A (Sigma Chemical Co.) and 2000 U/ml of RNase TI (Boehringer-Mannheim Corp.). Then, the mixture was incubated at 37° C. for 30 minutes. The incubated sample was extracted with a TE-saturated phenol/chloroform system and then with chloroform, and the water layer ultimately obtained was mixed with 1/10 volume of 3M sodium acetate solution (pH 5.2) and 2 volumes of ethanol. After maintenance at −80° C. for 30 minutes, the mixture was centrifuged at 12,000×g and at 4° C. for 15 minutes to recover a pellet which was then washed with 70% ethanol and dried. Thus obtained pellet of DNA (about 4 mg) was dissolved in 4 ml of TE for use in the following procedures.

(3) Preparation of DNA Fragment by PCR (polymerase chain reaction)

An appropriate DNA region containing BTG gene was isolated and amplified using a PCR technique (Saiki, R. F. et al., *Science*, vol. 230, pp. 1350–1354 (1985); and Mullis, K. B. and Faloona, F. A., *Methods in Enzymology*, vol. 155, pp. 335–350 (1987)).

(i) Synthesis of Primer DNA for PCR Use

Although BTG is known in the art, its amino acid sequence had not been known. The amino acid sequence of BTG was determined for the first time at Shimonishi Laboratory of Protein Engineering Research Institute, Osaka University in collaboration with the present inventors.

A DNA fragment was synthesized based on a base sequence deduced from a portion of the determined amino acid sequence (from 117 position phenylalanine to 123 position phenylalanine) of BTG. In this instance, DNA synthesis was carried out using a Cyclone Plus DNA Synthesizer manufactured by Milligen Biosearch.

The DNA fragment thus obtained was designated Primer #1 for use in the PCR synthesis, and its sequence is shown below.

$$5'\text{-TT}^T_C\ \text{GA}^T_C\ \text{GA}^A_G\ \text{GA}^A_G\ \text{AA}^A_G\ \text{GGI TT-3'}$$

(20 mer, 32 mix, I (inosine) = 1)

(SEQ ID NO: 9)

Another DNA fragment was prepared in the same manner based on a base sequence deduced from a portion of the amino acid sequence (from position 325 lysine to position 331 proline). The DNA fragment thus obtained was designated Primer #2 for use in the PCR synthesis, and its sequence is shown below.

$$5'\text{-GGC CAI CC}^T_C\ \text{TG}^T_C\ \text{TTI AC}^T_C\ \text{TT-3'}$$

(20 mer, 8 mix, I (inosine) = 2)

(SEQ ID NO: 10)

Each of the thus prepared DNA fragments was dissolved in TE to a concentration of 20 μM.

(ii) Amplification of DNA Fragment using PCR

The amplification reaction was carried out using GeneAmp ™ DNA Amplification Reagent Kit with AmpliTaq ™ (produced by Perkin-Elmer Japan) and DNA Thermal Cycler (DNA amplifier, Perkin-Elmer Japan). The composition of the reaction solution used is shown below.

|  |  | (final conc.) |
|---|---|---|
| H$_2$O | 53.5 μl |  |
| [10 x] Reaction Buffer (GeneAmp ™ DNA Amplification Reagent Kit with AmpliTaq ™) | 10 μl | [1 x] |
| dNTPs, Mix 1.25 mM | 16 μl | 200 μM |
| Primer #1 of (i) | 5 μl | 1.0 μM |
| Primer #2 of (i) | 5 μl | 1.0 μM |
| Template (BTG DNA 0.5 μg)* | 10 μl |  |
| AmpliTaq ™ DNA Polymerase | 0.5 μl | 2.5 U/assay |
| (total) | 100 μl |  |

After mixing 100 μl of the above reaction solution with 100 μl of mineral oil (Sigma Chemical Co.), a tube containing the resulting mixture was placed in the DNA Thermal Cycler (DNA amplifier, Perkin-Elmer Japan) to allow reaction under the following conditions.

| 95° C. | 1 min |
|---|---|
| 37° C. | 2 min |
| 72° C. | 3 min |

The reaction was repeated 35 cycles under these conditions and then the final reaction mixture was incubated at 72° C. for 7 minutes.

(iii) Recovery of Amplified DNA

After removing the mineral oil from the above reaction mixture, the remaining portion was mixed with 100 μl of chloroform and centrifuged at 15,000 rpm for 2 minutes using a centrifuge manufactured by Tomy Seiko Co., Ltd. to recover 100 μl of supernatant. Using a 10 μl portion of the supernatant, the size and the amount of the recovered DNA were measured using 1.5% agarose gel electrophoresis. As a result, it was confirmed that a 645 bp DNA fragment was amplified to a level of about 2 μg.

The remaining 90 μl portion of the supernatant was subjected to 1.5% low melting point agarose electrophoresis to cut out a band corresponding to 645 bp. The band was dissolved at 65° C. and mixed with the same volume of phenol. After centrifugation of the mixture, the resulting water layer was treated with phenol/chloroform and chloroform in that order. The thus treated water layer was mixed with 3M sodium acetate to a concentration of 8% and then with two volumes of ethanol, and the mixture was kept at −80° C. for 15 minutes. Thereafter, the mixture was centrifuged at 15,000 rpm and at 4° C. for 10 minutes to obtain a pellet which was then dissolved in 20 μl of water. In this manner, about 1 μg of DNA fragments was recovered.

(4) Structure of DNA Fragment Amplified by PCR

In order to determine whether the DNA fragment thus amplified by PCR was a part of BTG gene, direct sequencing was carried out using 0.4 μg of the DNA fragment in the following manner. In this instance, the above-described Primer #1 was used as a primer for the sequencing.

Materials (i) Reagents for DNA Sequencing

A sequencing kit, Sequenase ™ (version 2.0), manufactured by USB Corp., U.S.A., was used for the sequencing which was carried out basically by the dideoxy method (F. Sanger et al., *J. Mol. Biol.*, 143, 161 (1980)).

(ii) Labeling of Primer for Sequencing Use

Using a 2 pmol portion of Primer #1 prepared as in the foregoing for PCR reaction, its 5' end was labeled with [$^{32}$P] making use of T4 Kinase (TOYOBO Co., Ltd.). In this instance, [γ-$^{32}$P] ATP having a specific activity of 3000 Ci/mmol was used. Free [γ-$^{32}$P] ATP remaining in the labeled primer was removed by passing the product through an appropriate mini column (Sephadex G-50 DNA Grade Fine (Pharmacia)).

(iii) Reaction Solution (3.25 μl in total) for Sequencing

Using the Sequenase ™ kit, the following reaction mixture was prepared in each of four tubes for use in a G, A, T and C reaction.

| 2.5 μl | G, A, T, C termination mix |
|---|---|
| 0.38 μl | 5 × buffer (Sequenase ™ (version 2.0)) |
| 0.22 μl | 0.1 M DTT |
| 0.15 μl | Sequenase (2 units) |

Reaction (i) A 0.4 μg portion of the amplified DNA and 2 pmol of [$^{32}$P]-labeled primer were dissolved in 12 μl of TE, and the solution was heat denatured at 95° C. for 5 minutes, followed by rapid cooling in an ice bath.

(ii) Immediately after cooling, each of the four tubes was charged with 2.8 μl of the solution thus prepared in (i) above and then with 3.25 μl of corresponding sequence reaction solution (Sequenase ™ (version 2.0)). After incubation of the thus prepared tubes at 37° C. for 10 minutes, the reaction was terminated by adding 4 μl of a termination solution (Sequenase ™ (version 2.0)) and heating at 75° to 80° C. for 2 minutes, and the resulting samples were electrophoresed using a sequencing gel.

As a result of the direct sequencing, a base sequence encoding a portion of the amino acid sequence of BTG (from 129 position valine to 149 position asparagine) was found in the DNA fragment. As a result, this DNA fragment was considered to be a part of the BTG gene.

(5) Subcloning of PCR-Amplified DNA Fragment into pUC 19

Next, the DNA fragment amplified by PCR was subcloned into the SmaI site of pUC 19. For this purpose, both termini of the DNA fragment were made blunt-ended using the following procedure with a DNA Blunting Kit (Takara Shuzo Co., Ltd.).

(i) A micro-centrifugation tube was charged with a total of 9 µl of the following reaction solution.

| DNA Fragment | 8 µl (0.4 µg) |
| 10 × Buffer | 1 µl |

(ii) In order to prevent annealing at the DNA termini, the thus prepared tube was incubated at 70° C. for 5 minutes and then transferred in a 37° C. incubator.

(iii) A 1 µl portion of T4 DNA polymerase was transferred into the tube and the contents in the tube were mixed gently by pipetting.

(iv) The resulting mixture in the tube was incubated at 37° C. for 5 minutes.

(v) A DNA dilution buffer (DNA Blunting Kit, Takara Shuzo Co., Ltd.) was added to the thus incubated mixture to a final concentration of 1 µg DNA/50 µl and the resulting mixture was stirred vigorously using a vortex mixer.

The thus blunt-ended DNA fragment was ligated with a SmaI digest of pUC 19, and E. coli DH 5α was transformed with the resulting ligate in the presence of 5-bromo-1-chloro-3-indolyl-β-D-galactoside (X-gal) and isopropyl-β-D-thiogalactoside (IPTG). A plasmid was isolated from an ampicillin-resistant white colony, in which the PCR-amplified DNA fragment was incorporated into the SmaI site of pUC 19. This plasmid was designated pUC 19 BTG and used in the following procedures. In this instance, ligation was carried out using a DNA Ligation Kit manufactured by Takara Shuzo Co., Ltd.

Next, in order to determine even wider range of the base sequence of the PCR-amplified DNA fragment, DNA sequencing was carried out using the thus obtained plasmid pUC 19 BTG as a template using a conventional method in which 7-deaza dGTPλ Sequenase kit of USB Corp. was used. As a result, a base sequence consisting of 564 base pairs was determined as shown in Table 9 below.

TABLE 9

TCCGTGATGAACAGGGCCCTGGAGAACGCCCACGACGAGAGCGCTTACCTCGACAA

CCTCAAGAAGGAACTGGCGAACGGCAACGACGCCCTGCGCAACGAGGACGCCCGTT

CCCCGTTCTACTCGGCGCTGCGGAACACGCCGTCCTTTAAGGAGCGGAACGGAGGC

AATCACGACCCGTCCAGGATGAAGGCCGTCATCTACTCGAAGCACTTCTGGAGCGG

CCAGGACCGGTCGAGTTCGGCCGACAAGAGGAAGTACGGCGACCCGGACGCTTTCC

GCCCGGCCCCCGGGACCGGCCTGGTCGACATGTCGAGGGACAGGAACATTCCGCGC

AGCCCCACCAGCCCCGGTGAGGGATTCGTCAATTTCGACTACGGCTGGTTCGGCGC

CCAGACGGAAGCGGACGCCGACAAGACCGTCTGGACCCACGGAAATCACTATCACG

CGCCCAATGGCAGCCTTGGTGCCATGCATGTATACGAGAGCAAGTTCCGCAACTGG

TCCGAAGGTTACTCCGACTTCGACCGCGGAGCCTATGTGATCACCTTCATCCCCAA

GAGC (SEQ ID NO: 11)

(6) Preparation of DNA Library (6-1) Partial Digestion of Chromosomal DNA of Streptoverticillium sp.

(a) A mixture of 24 µg of chromosomal DNA and 60 µl of BamHI 10×buffer (10×High Buffer of TOYOBO Co., Ltd.) was adjusted with sterile water to a total volume of 594 µl.

(b) The resulting mixture was pre-heated at 37° C. for 5 minutes.

(c) The thus pre-heated mixture was further mixed with 6 µl of BamHI (TOYOBO Co., Ltd.) and the resulting mixture was incubated at 37° C. for 10 minutes to complete the restriction enzyme reaction.

(d) The reaction was terminated by inactivating the restriction enzyme by heating the reaction mixture at 65° C. for 15 minutes.

(6-2) Cloning (using EMBL3 Cloning Kit of Stratagene Cloning Systems)

(i) Ligation (a) A 25 µl portion of the partially digested DNA obtained as described above was subjected to ethanol precipitation and the resulting precipitate was dissolved in 2.5 µl of TE.

(b) To this was added 1.0 µl of EMBL3 pre-digested arms (1 µg/µl), 0.5 µl of 10×ligation buffer, 0.5 µl of 10 mM ATP (pH 7.5) and 0.5 µl of T4 DNA ligase (8 units/µl, product of Boehringer-Mannheim Corp.). After mixing, ligation was carried out at 4° C. overnight. In this instance, the 10×ligation buffer consisted of 500 mM Tris-HCl (pH 7.5), 70 mM MgCl₂ and 10 mM DTT.

(ii) Packaging (using Gigapack II Gold Packaging Extract, produced by Stratagene Cloning Systems)

(a) Appropriate portions of the sonic extract and freeze thaw lyzate of the packaging kit stored in a freezer (−70° C.) were put on dry ice, and the sonic extract was allowed to start melting.

(b) The freeze thaw lyzate was warmed until it started to melt between the fingers.

(c) After adding 4 μl (1.6 μg on a DNA basis) of the above-described DNA solution, the freeze thaw lyzate was put on an ice bath.

(d) Immediately thereafter, 15 μl of the sonic extract was added to the DNA-containing freeze thaw lyzate.

(e) The resulting mixture was stirred to be mixed thoroughly without causing foams.

(f) The mixture was centrifuged at 4,000×g for 5 seconds to precipitate all of the contents of the mixture in the tube.

(g) The resulting tube was incubated at room temperature (22° C.) for 2 hours.

(h) To this was added 500 μl of a phage dilution buffer (prepared by dissolving 5.8 g of NaCl, 2.0 g of $MgSO_4$, 50 ml of 1M Tris-HCl, pH 7.5, and 5 ml of 2% gelatin in 1 liter of water, followed by autoclaving).

(i) After adding 20 μl of chloroform, the resulting sample was mixed gently.

(j) The resulting mixture was centrifuged at 4,000×g for 5 seconds to precipitate debris.

(k) The supernatant thus collected was stored at 4° C.

(iii) Plating (a) *E. coli* P2392 was inoculated into TB medium which consisted of 5 g/l of NaCl and 10 g/l of Bactotryprone. Strain P2392 has the following properties: hsdR 514 (rk−, mk+), supE 44, supF 58, lacY 1, or Δ (lacIZY), galK 2, galT 22, metB 1, trpR 55, (P2).

(b) P2392 thus inoculated in TB medium was cultured at 37° C. with shaking.

(c) When the turbidity at $OD_{600}$ reached 0.5, the cells were collected by centrifugation at 1,100×g for 15 minutes at room temperature, and subsequently suspended in an appropriate volume of 10 mM $MgSO_4$ solution to adjust the turbidity of the suspension to $OD_{600}=0.5$.

(d) The resulting cell suspension was mixed with a small portion of the supernatant obtained in (ii)-(k) above and incubated at 37° C. for 15 minutes.

(e) The resulting suspension was mixed with 8 ml of a top agar which has been melted and warmed in advance, and the mixture was overlaid on an NZY plate.

Top Agar: NaCl 5 g/l, $MgSO_4.H_2O$ 2 g/l, Yeast Extract 5 g/l, NZ Amine 10 g/l, Agarose 0.7%

NZY Plate: NaCl 5 g/l, $MgSO_4.H_2O$ 2 g/l, Yeast Extract 5 g/l, NZ Amine 10 g/l, Agar 15 g/l (f) The resulting plate was incubated overnight at 37° C.

As a result, a library of $3.0 \times 10^4$ independent clones was obtained.

(7) Screening of BTG Gene

Cloning of BTG gene was carried out using the library obtained in (6). Firstly, plating of phages in the library was carried out in the same manner as the procedure in (6)-(iii). After culturing overnight at 37° C., lifting of phages was carried out from the thus formed plaques in the following manner.

(a) Each plate was maintained at 4° C. for a few hours.

(b) A nitrocellulose filter (S & S) was superposed on the surface of the plate (surface of the top agar).

(c) The thus filter-covered plate was maintained as it is for about 2 minutes.

(d) The nitrocellulose filter was removed from the plate and soaked for 1 minute in a solution which consisted of 0.5M NaOH and 1.5M NaCl.

(e) The thus treated nitrocellulose filter was soaked for 5 minutes in a solution which consisted of 1.5M NaCl and 1.M Tris-HCl (pH 7.5).

(f) The resulting nitrocellulose filter was then soaked for 30 seconds in 2×SSC (1×SSC consists of 0.15M NaCl and 0.015M sodium citrate and has a pH value of 7.0).

(g) The thus soak-treated nitrocellulose filter was air-dried on a 3 MM filter paper.

(h) The nitrocellulose filter thus dried was held between two 3 MM filter papers and baked at 80° C. for 2 hours.

Followed by phage lifting performed in this manner, hybridization was carried out using a probe which had been prepared by isolating a 650 bp fragment from EcoRI-HindIII digests of the plasmid pUC 19 BTG obtained in the foregoing manner and labeling the fragment with $^{32}P$. This 650 bp fragment contained the entire portion of the DNA fragment which had been amplified by PCR. The $^{32}P$-labeling was carried out using a multi-prime DNA labeling set manufactured by Amersham. The specific activity of the thus prepared probe was found to be $3 \times 10^8$ cpm/μg DNA. Hybridization was carried out under the following conditions.

Pre-Hybridization:

Overnight incubation at 42° C. in a hybridization solution consisting of 50% formamide, 1×Denhanvits (0.02% BSA, 0.02% Ficoll, 0.02% polyvinyl pyrrolidone), 0.1% SDS, 50 mM sodium phosphate buffer (pH 6.5) and 200 μg/μl denatured salmon sperm DNA.

Hybridization:

Overnight incubation at 42° C. in the hybridization solution in the presence of 2 ng/ml of the probe.

Washing:

1. 2×SSC, 0.1% SDS, 5 minutes×3 times, room temperature 2. 1×SSC, 0.1% SDS, 1 hour×2 times, 68° C.

After washing, the nitrocellulose filter was air-dried and subjected to autoradiography.

By carrying out these steps, a total of about 40,000 plaques were screened (first screening) which resulted in the isolation of 16 clones having strong signals. Each of these clones was further subjected to a second screening to purify it into a single plaque. As a result, a total of 6 single plaque clones having strong signals were obtained.

(8) Structural Analysis of Cloned DNA

In order to examine the DNA structures of the thus obtained 6 clones, DNA fragments were prepared from these clones in accordance with the method disclosed in Maniatis, *Molecular Cloning*, a Laboratory Manual, 2nd Edition.

Restriction enzyme digestion maps of the DNA fragments thus prepared were drawn up using restriction enzymes BamHI, SphI, NcoI, BglII and KpnI (all purchased from TOYOBO Co., Ltd.). As a result, it was found that these clones contained almost the same DNA fragment, and the restriction enzyme digestion map of the fragment was determined as follows.

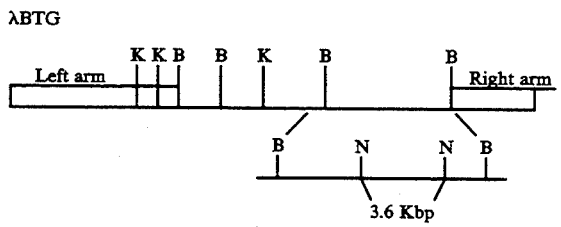

K: KpnI, B: BamHI, N: NcoI

Next, Southern hybridization was carried out by digesting the DNA fragment with each restriction enzyme, isolating the digested fragments by electrophoresis, fixing the isolated fragments on a nitrocellulose filter and then hybridizing the fixed fragments with the probe used in the above-described BTG gene screening. The same hybridization conditions used for the screening of BTG gene were employed.

As a result, it was found that the 3.6 Kbp NcoI fragment of the above-described restriction enzyme digestion map hybridized with the probe and showed a strong signal. As a consequence, it was concluded that at least a portion of the BTG gene is contained in the NcoI fragment.

(9) Subcloning of 3.6 Kbp NcoI Fragment

Next, an attempt was made to subclone the 3.6 kbp NcoI fragment into a plasmid. The DNA fragment of the phage clone obtained as described above was digested with NcoI and a 3.6 Kbp DNA fragment was recovered by using a low melting point agarose. The thus obtained NcoI fragment was ligated with a DNA fragment which had been prepared by digesting plasmid pTV118N (Takara Shuzo Co., Ltd.) with NcoI, and *E. coli* DH 5α was transformed with the thus ligated DNA sample. By culturing a transformant obtained in this way, a plasmid designated pTV118 NcoI was recovered in which the 3.6 kbp NcoI fragment had been subcloned into pTV118N.

(10) DNA Sequencing of BTG Gene

DNA sequencing was carried out using the thus obtained plasmid pTV118 NcoI as a template by repeating the process described in (4) above except that the reaction temperature was changed to 48° C. and, depending on the degree of compression of the sequence, SSB (single stranded DNA binding protein, TOYOBO Co., Ltd.) was added to the reaction system. The base sequence thus determined is shown in the Table 10 below.

TABLE 10

TGCGGCGACGCGTAGGCAATGGGGGTTCATCGCGACGTGCTTCCGCACGGCCGCGT
1
TCAACGATGTTCCACGACAAAGGAGTTGCAGGTTTCCATGCGCTATACGCCGGAGG

CTCTCGTCTTCGCCACTATGAGTGCGGTTTATGCACCGCCGGATTCATGCCGTCGG

CCGGCGAGGCCGCCGCCGACAATGGCGCGGGGGAAGAGACGAAGTCCTACGCCGAA

ACCTACCGCCTCACGGCGGATGACGTCGCGACATCAACGCGCTCAACGAAGCGCTC

CGGCCGCTTCGAGCGCCGGCCCGTCGTTCCGGGCCCCCGACTCCGACGACAGGGTC

ACCCCTCCCGCCGAGCCGCTCGACAGGATGCCCGACCCGTACCGTCCCTCGTACGG

CAGGGCCGAGACGGTCGTCAACAACTACATACGCAAGTGGCAGCAGGTCTACAGCC

ACCGCGACGGCAGGAAGCAGCAGATGACCGAGGAGCAACGGGAGTGGCTGTCCTAC

GGCTGCGTCGGTGTCACCTGGGTCAATTCGGGTCAGTACCCCACGAACAGACTGGC

CTTCGCGTCCTTCGACGAGGACAGGTTCAAGAACGAGCTGAAGAACGGCAGGCCCC

GGTCCGGCGAGACGCGGGCGGAGTTCGAGGGCCGCGTCGCGAAGGAGAGCTTTGAT

GAAGAGAAGGGGTTCCAGCGGGCGCGTGAGGTGGCGTCCGTGATGAACAGGGCCCT

GGAGAACGCCCACGACGAGAGCGCTTACCTCGACAACCTCAAGAAGGAACTGGCGA

ACGGCAACGACGCCCTGCGCAACGAGGACGCCCGTTCCCCGTTCTACTCGGCGCTG

CGGAACACGCCGTCCTTTAAGGAGCGGAACGGAGGCAATCACGACCCGTCCAGGAT

GAAGGCCGTCATCTACTCGAAGCACTTCTGGAGCGGCCAGGACCGGTCGAGTTCGG

CCGACAAGAGGAAGTACGGCGACCCGGACGCTTTCCGCCCGGCCCCGGGACCGGC

CTGGTCGACATGTCGAGGGACAGGAACATTCCGCGCAGCCCCACCAGCCCCGGTGA

GGGATTCGTCAATTTCGACTACGGCTGGTTCGGCGCCCAGACGGAAGCGGACGCCG

ACAAGACCGTCTGGACCCACGGAAATCACTATCACGCGCCCAATGGCAGCCTTGGT

GCCATGCATGTATACGAGAGCAAGTTCCGCAACTGGTCCGAAGGTTACTCCGACTT

CGACCGCGGAGCCTATGTGATCACCTTCATCCCCAAGAGCTGGAACACCGCCCCCG
1218
ACAAGGTAAAGCAGGGCTGGCCGTGATGTGAGCG (SEQ ID NO: 12)

The initiation codon of BTG gene was estimated to be the ATG moiety indicated as position 1 in the above base sequence, on the basis of the following three points: (1) a stop codon exists 81 bases upstream of position 1 and therefore the open reading frame of the BTG gene appears to start at downstream from this position; (2) a typical SD sequence (5'AAAGGAG-3') exists 13 bases upstream of the position 1 ATG; and (3) a region of about 20 amino acids from the position 1 ATG methionine is a signal sequence-like moiety which is relatively rich in hydrophobic amino acids.

In addition, since a stop codon exists at position 1219 on the 3' end side, the position 1216 proline can be regarded as the C-terminus of the BTG gene. In the open reading frame deduced from the base sequence, the N-terminal amino acid of BTG determined by amino acid sequencing corresponds to the position 226 aspartic acid. As a result, it was found that the open reading frame of the BTG gene deduced herein had a structure consisting of the structure determined by the amino acid sequencing and additional 75 amino acids as follows:

EXAMPLE 2

Chemical Synthesis of BTG Gene

Design and Synthesis of BTG Gene

BTG gene DNA was designed based on the complete amino acid sequence thus determined by the foregoing analysis. In this instance, the utilization frequency of codons in *E. coli*, yeast and the like (Ikemura, T. and Ozeki, H., *Cold Spring Harbor Symp. Quant. Biol.*, vol. 47, p. 1087 (1983)) was taken into consideration, and restriction enzyme recognition sites were arranged on DNA chains of both ends of each of the fragments (1) to (5) for use in ligation of these fragments.

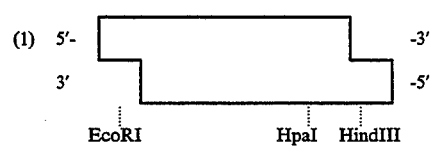

TABLE 11

| −75 | −70 | −60 | −50 |
|---|---|---|---|
| M R Y T P | E A L V F A T M S A | V Y A P P D S C R R | P A R P P P T M A R |

| −40 | −30 | −20 | −10 |
|---|---|---|---|
| G K R R S P T P K P | T A S R R M T S R H | Q R A Q R S A P A A | S S A G P S F R A P |

| 10 | 20 | 30 | 40 |
|---|---|---|---|
| D S D D R V T P P A | E P L D R M P D P Y | R P S Y G R A E T V | V N N Y I R K W Q Q |

| 50 | 60 | 70 | 80 |
|---|---|---|---|
| V Y S H R D G R K Q | Q M T E E Q R E W L | S Y G C V G V T W V | N S G Q Y P T N R L |

| 90 | 100 | 110 | 120 |
|---|---|---|---|
| A F A S F D E D R F | K N E L K N G R P R | S G E T R A E F E G | R V A K E S F D E E |

| 130 | 140 | 150 | 160 |
|---|---|---|---|
| K G F Q R A R E V A | S V N M R A L E N A | H D E S A Y L D N L | K K E L A N G N D A |

| 170 | 180 | 190 | 200 |
|---|---|---|---|
| L R N E D A R S P F | Y S A L R N T P S F | K E R N G G N H D P | S R M K A V I Y S K |

| 210 | 220 | 230 | 240 |
|---|---|---|---|
| H F W S G Q D R S S | S A D K R K Y G D P | D A F R P A P G T G | L V D M S R D R N I |

| 250 | 260 | 270 | 280 |
|---|---|---|---|
| P R S P T S P G E G | F V N F D Y G W F G | A Q T E A D A D K T | V W T H G N H Y H A |

| 290 | 300 | 310 | 320 |
|---|---|---|---|
| P N G S L G A M H V | Y E S K F R N W S E | G Y S D F D R G A Y | V I T F I P K S W N |

| 330 | | | |
|---|---|---|---|
| T A P D K V K Q G W | P | | |

(SEQ ID NO: 13)

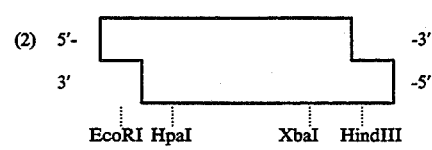

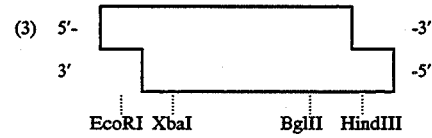

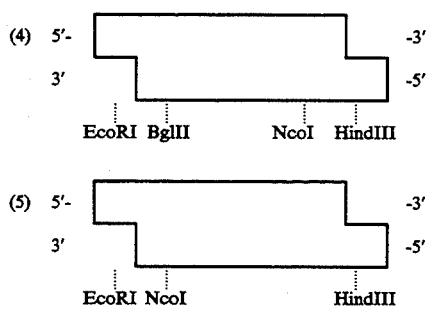

(4) EcoRI BglII NcoI HindIII (5) EcoRI NcoI HindIII

Next, the thus designed gene DNA was subjected to chemical synthesis by phosphoamidite technique using DNA Synthesizer 380A manufactured by Applied Biosystems.

The length of one DNA chain was set at around 30 to 40 bases, judging from the reliability and workability of currently used DNA synthesizers and DNA purification techniques. Since BTG consists of 331 amino acids, its corresponding gene requires at least 993 bases. Also, it is necessary to synthesize twice the amount of the gene DNA because the DNA must be incorporated into a plasmid as a double-stranded chain. In practice, however, it is necessary to introduce further a termination codon and restriction enzyme recognition sites for the ligation of each fragment. As a result, a total of 54 DNA chains as 27 pairs of double strands were synthesized. In addition, since the base sequence of the DNA chain must be confirmed after its incorporation into a plasmid, it may be convenient from handling point of view to split the DNA into several fragments (about 200 bp for each) and incorporate such into respective plasmids, so that the base sequence can be determined safely.

In this procedure, therefore, the DNA chain was separated into 5 blocks each consisting of about 200 base pairs, the base sequence of each block incorporated into a plasmid was confirmed and then the complete BTG gene was constructed.

Construction of Synthetic Type BTG Gene

Firstly, construction of each fragment (about 200 bp) of the 5 blocks was carried out. Since the 5' end of a chemically synthesized oligonucleotide does not have phosphoric acid, phosphorylation of the 5' end was carried out using polynucleotide kinase. In this instance, phosphorylation of DNA chains on both 5' ends of each fragment was carried out after ligation.

| | |
|---|---|
| 100 pmol Oligonucleotide (dissolved in water) | 7.5 μl |
| 10 × Buffer* | 1 μl |
| 10 mM ATP | 1 μl |
| Polynucleotide Kinase (Takara Shuzo Co., Ltd.) | 0.5 μl (5 units) |
| (total) | 10 μl |

*10 × buffer consisted of 650 mM Tris-HCl (pH 7.6), 100 mM MgCl$_2$, 150 mM dithiothreitol and 10 mM spermidine.

The above composition was transferred into an Eppendorf tube and incubated at 37° C. for 1 hour and then boiled for 3 minutes to inactivate the enzyme. Next, a mixture of 5 μl of a fragment with the same volume of its complementary fragment (10 μl in total) was incubated at 90° C. for 3 minutes in a water bath and then the water temperature in the bath was lowered spontaneously to 37° C. to complete annealing. Thereafter, two DNA fragments (20 μl) were ligated together.

| | |
|---|---|
| Two DNA Fragment Pairs | 20 μl |
| 150 mm Dithiothreitol (DTT) | 2 μl |
| 10 mM ATP | 2 μl |
| Cloned T4 DNA Ligase (Takara Shuzo Co., Ltd.) | 0.5 μl (150 units) |
| (total) | 24.5 μl |

The above composition was transferred into an Eppendorf tube and incubated at 16° C. for 30 minutes. A 22 μl portion of the resulting reaction solution was mixed with the same volume of an additional two reaction solutions obtained in the same manner (66 μl in total), and 0.5 μl of ligase was added to the mixture. After incubating the mixture at 16° C. for 30 minutes, the resulting ligation solution was subjected to 10% polyacrylamide gel electrophoresis to recover a DNA fragment consisting of about 200 base pairs.

Each of the thus constructed DNA fragments (1) to (5) had an EcoRI recognition site on its 5' end and a HindIII recognition site on the 3' end. After phosphorylating both 5' ends of each DNA fragment, the resulting fragment was mixed with a plasmid pUC 18 (Yanisch-Perron, C. et al., Gene, vol. 33, p. 103 (1985)) which had been digested with EcoRI and HindIII in advance, and the mixture was subjected to a ligation reaction at 16° C. for 1 hour using a DNA Ligation Kit (Takara Shuzo Co., Ltd.).

Next, E. coli JM 109 strain was transformed with each of the thus prepared ligation mixtures. This strain, JM 109, has the following characteristics: recA 1, Δ lac-pro, endA 1, gryA 96, thi-1, hsdR 17, supE 44, relA 1, λ−, (F'traD 36, proAB, lacIqZΔM15).

E. coli JM 109 strain is a strain which makes possible easy selection of recombinants when transformation of pUC-based plasmid DNA or transduction of M13 phage vector DNA is carried out, making use of reactivation of β-galactosidase by the action of lacZ α peptide produced by a vector DNA and lacZ Δ M15 encoded by JM 109 F'. In other words, when JM 109 strain is cultured on a medium containing IPTG (isopropyl-β-D-thiogalactopyranoside) and X-Gal (5-bromo-4-chloro-3-indole-β-D-galactoside), this strain forms a blue colony when it contains plasmid pUC 18 thus showing the presence of β-galactosidase activity, while this strain forms white colony when it contains a recombinant plasmid in which a foreign DNA fragment is incorporated because of its inability to reactivate β-galactosidase activity.

Plasmids were recovered from several white colonies and their DNA sequences were determined in accordance with the method of Sanger, F. et al., J. Mol. Biol., vol. 143, p. 161 (1980). In this way, clones of interest were selected in which each inserted fragment showed the correct base sequence as has been designed.

Next, ligation of these DNA fragments was carried out making use of their respective restriction enzyme recognition sites.

Firstly, ligation of fragments (2) with (3) was carried out using BTG gene-containing ScaI-XbaI fragments after digesting these fragments with ScaI and XbaI making use of the ScaI recognition site in the ampicillin resistant gene of pUC 18. In the same manner, ligation of fragments (4) with (5) was carried out using BTG gene-containing ScaI-NcoI fragments after digesting these fragments with ScaI and NcoI. Ligation of fragments (2), (3), (4) and (5) was carried out using BTG gene-containing ScaI.BglII fragments after digesting the thus ligated products of (2) and (3) and of (4) and (5) with ScaI and BglII.

Finally, an EcoRI.HpaI fragment of the DNA fragment (1) and a HpaI.HindIII fragment of the thus ligated sample of fragments (2), (3), (4) and (5) were mixed with a high expression/secretion vector for *E. coli* use, pIN-III-ompA2 (Ghrayeb, J. et al., *EMBO J.*, vol. 3, p. 2437 (1984)), which had been digested with EcoRI and HindIII in advance, and the resulting mixture was subjected to a ligation reaction at 16° C. for 30 minutes using a DNA Ligation Kit (Takara Shuzo Co., Ltd.). The resulting reaction mixture was then incorporated into *E. coli* JA 221 strain (hsdM+, trpE 5, leuB 6, lacY, recA/F', lacI$^q$, lac+, pro+) (Nakamura, K. et al., *J. Mol. Appl. Genet.*, vol. 1, p. 289 (1982)). After culturing the thus treated cells, several plasmids were recovered from formed colonies, and examined as to whether the BTG gene (about 1 kb) was inserted correctly. A vector for use in the expression and secretion of BTG thus obtained was designated pOMPA-BTG. The base sequence of the chemically synthesized BTG gene, inserted into pIN-III-ompA2, is shown in Table 2.

The plasmid pIN-III-ompA2 used in this example contained a promoter ($lpp^p$) of *E. coli* outer membrane lipoprotein, a promoter and an operator ($lac^{po}$) of lactose operon and a region for the signal peptide of *E. coli* outer membrane protein OmpA. As a result, expression of a gene incorporated into a downstream moiety of these regions is induced by the addition of IPTG, and the resulting genetic product is accumulated in the periplasm. Significant amounts of genetic products in the periplasm have been reported, for instance, by Ikemura, H. et al., *J. Biol. Chem.*, vol. 262, p. 7859 (1987) and Hsiung, H. M. et al., *Bio/Technology*, vol. 4, p. 991 (1986). Purification of BTG protein may be effected by the conventional means of extracting periplasmic protein molecules making use of the osmotic pressure shock technique (Koshland, D. et al., *Cell*, vol. 20, p. 749 (1980) and then purifying the BTG protein by various biochemical techniques such as ammonium sulfate precipitation, ion exchange chromatography, gel filtration, HPLC and the like.

Not only pIN-III-ompA but also other expression plasmids may be used as the plasmid for use in the expression of the synthesized BTG gene. These other expression plasmids may easily be selected by those skilled in the art depending on the expression system to be used. For example, when an *E. Coli* strain is used as the host cell, commonly used vectors such as pTrc99A (Pharmacia); pPROK-C and pKK233-2 (Clontech Co.); and pNH8a, pNH16a, pNH18a, pcDNAII, and pAX (Stratagene) can be used for the construction of an expression secretion vector of the present invention.

EXAMPLE 3

Expression of Synthetic BTG Gene

An *E. coli* JA 221 strain containing plasmid pOMPA-BTG in which the synthetic BTG gene had been incorporated (*E. Coli* AJ12569; BP-3558) was cultured in M9 casamino acid medium supplemented with 50 μg/ml of ampicillin at 37° C. for 2 hours with shaking, followed by additional culturing at 23° C. for 4 hours in the presence of 1 mM IPTG. Cells were collected from 50 ml of the thus cultured broth by centrifugation and suspended in 2.5 ml of a solution consisting of 20% sucrose and 10 mM Tris-HCl (pH 7.5) to which was then added 0.125 ml of 0.5M EDTA (pH 8.0). After keeping on ice for 30 minutes, the resulting cell suspension was centrifuged at 12000 rpm for 10 minutes to separate supernatant from cells. The resulting pellet or cells were suspended in 3 ml of distilled water, kept for 30 minutes on ice and then centrifuged at 12000 rpm for 10 minutes to separate supernatant from the cells. These supernatants were combined and ultracentrifuged at 38000 rpm for 60 minutes. The resulting supernatant was used as a periplasm fraction.

The cells remaining after centrifugation were suspended in 3 ml of distilled water, the suspension was subjected to ultrasonic disintegration (200 W, 5 minutes) and the resulting sample was used as a cytoplasm fraction.

Measurement of BTG Activity in Each Fraction

The BTG activity in each of the thus prepared fractions (culture filtrate, periplasm fraction and cytoplasm fraction) was measured using the hydroxamic acid method (colorimetric hydroxamate procedure according to the method of Folk and Cole).

The measurement was carried out, basically, according to the method of Folk and Cole (colorimetric hydroxamate procedure) disclosed in *J. Biol. Chem.*, vol. 241, p. 5518, (1966). That is, the reaction was carried out using benzyloxycarbonyl-L-glutamylglycine (CBZ-gln-gly) and hydroxylamine as the substrates in the presence or absence of $Ca^{2+}$. Hydroxamic acid thus formed was made into an iron complex in the presence of trichloroacetic acid. Thereafter, absorption of the iron complex was measured at 525 nm and the amount of hydroxamic acid was obtained from a calibration curve to calculate the activity of the sample.

<Measurement of Activity>

| | |
|---|---|
| Reagent A | |
| 0.2 M Tris-HCl Buffer (pH 6.0) | |
| 0.1 M Hydroxylamine | |
| 0.05 M Calcium Chloride | |
| 0.01 M Reduced Form Glutathione | |
| 0.03 M CBZ-gln-gly (Kokusan Kagaku Co., Ltd.) | |
| Reagent B | |
| 3 N HCl | 1 volume |
| 12% Trichloroacetic Acid | 1 volume |
| 5% $FeCl_3.6H_2O$ (dissolved in 0.1 N HCl) | 1 volume |

A 0.4 ml portion of a sample (BTG as the enzyme solution) was mixed with 0.4 ml of Reagent A. After incubating the mixture at 37° C. for 10 minutes, 0.4 ml of Reagent B was added to the resulting mixture to terminate the reaction and form an iron complex. Thereafter, absorption of the complex was measured at 525 nm.

As a control, an enzyme solution was inactivated by heating and subjected to the same reaction procedure, and its absorbance at 525 nm was subtracted from that of the active enzyme solution. A calibration curve was prepared using the same procedure except that γ-monohydroxamic acid L-glutamate was used instead of the enzyme solution. The amount of hydroxamic acid formed was calculated from the corrected absorbance using the thus prepared calibration curve. In this instance, one unit of the enzyme activity was defined as the amount of enzyme catalyzing the formation of one micromole of hydroxamic acid per minute under the above-described reaction conditions.

The following table shows the results obtained.

| Samples | IPTG (mM) | BTG Activity (U/mg protein) |
|---|---|---|
| Culture Filtrate | — | 0 |
| | 1 | 0.025 |
| Periplasm Fraction | — | 0 |
| | 1 | 0.22 |
| Cytoplasm Fraction | — | 0 |
| | 1 | 0.033 |

Though not so significant, BTG activities were detected in each of the samples when induced with IPTG.

In order to confirm the formation of the BTG gene product, an anti-BTG antibody was prepared in a rabbit using purified BTG and Western blotting was carried out making use of Vectastain ABC kit, produced by Vector Laboratories, Inc. in the following manner.

A 0.5 μl portion of each protein fraction was subjected to SDS-polyacrylamide gel electrophoresis and the resulting gel was transferred on a membrane filter (Immobilon, manufactured by Millipore Corp.) to fix the antigen protein on the filter. Thereafter, Western blotting was carried out using the rabbit anti-BTG antibody (1000 times dilution of a stock having an antibody titer of 64) to confirm product of the BTG gene at the protein level.

In this instance, the protein samples were applied to the SDS-polyacrylamide gel in the following order or lanes.

1: purified BTG (control)
2: culture filtrate (IPTG not added)
3: culture filtrate (IPTG 1 mM added)
4: periplasm fraction (IPTG not added)
5: periplasm fraction (IPTG 1 mM added)
6: cytoplasm fraction (IPTG not added)
7: cytoplasm fraction (IPTG 1 mM added)

As a result, colored bands were observed at the same position in lanes 1, 3, 5 and 7. In other words, protein reacted with the anti-BTG antibody was detected in every IPTG-added fraction at the same position which was equivalent to the molecular weight of the purified BTG.

Thus, it is apparent, in accordance with the present invention, a DNA gene has been provided which encodes transglutaminase, a plasmid in which the gene is incorporated, a transformant transformed with the plasmid and a process for the production of transglutaminase that comprises culturing the transformant.

EXAMPLE 4

Expression of BTG Gene (natural) in Actinomycetes (1) Preparation of Plasmid Vector (pIJ 702)

Streptomyces lividans 3131 ATCC 35287 containing a plasmid pIJ 702 was cultured at 30° C. for 2 days using the following medium.

| YEME medium + 0.5% glycine + 50 μg/ml thiostrepton | |
|---|---|
| 0.3% | Yeast Extracts |
| 0.5% | Peptone |
| 0.3% | Malt Extracts |
| 0.1% | Magnesium Chloride |
| 1.0% | Glucose |
| 34.0% | Sucrose |
| 0.5% | Glycine |
| 0.1% | 50 mg/ml thiostrepton solution (sigma Chemical Co.; dimethyl sulfoxide solution) |

-continued

| YEME medium + 0.5% glycine + 50 μg/ml thiostrepton |
|---|
| (total 1 liter, pH 7.0) |

A 200 ml portion of the thus cultured broth was centrifuged at 12,000×g and at 4° C. for 10 minutes, and the resulting pellet (cells) was washed by suspending the cells in a solution consisting of 50 mM Tris-HCl (pH 8.0), 5 mM EDTA and 50 mM NaCl and centrifuging at 13,000×g for 5 minutes at room temperature. The thus washed cells were suspended in 10 ml of a solution consisting of 50 mM Tris-HCl (pH 8.0), 10 mM EDTA and 25% sucrose (hereinafter, referred to as "TE-Sucrose"). The resulting cell suspension was mixed with 2 ml of TE-Sucrose containing 30 mg/ml of lysozyme (Sigma Chemical Co.) and 4 ml of 0.25M EDTA, and the mixture was incubated at 37° C. for 30 minutes. To this were then added 2 ml of 20% SDS and 5 ml of 5M NaCl in that order. After stirring gently, the resulting mixture was incubated overnight at 0° C. The resulting cell lysate was centrifuged at 100,000×g and at 4° C. for 40 minutes, and the supernatant thus obtained was mixed with a 30% solution of polyethylene glycol 6000 (final concentration, 10%). After incubating at 0° C. for 4.5 hours, the resulting mixture was centrifuged at 900×g and at 4° C. for 5 minutes, and the precipitate thus obtained was dissolved in a solution consisting of 10 mM Tris-HCl (pH 8.0), 1 mM EDTA and 50 mM NaCl. To this were added 16.8 g of cesium chloride and 1.2 ml of a solution consisting of 10 mM Tris-HCl (pH 8.0) and 1 mM EDTA (hereinafter, referred to as "TE") in which ethidium bromide has been dissolved to a concentration of 10 mg/ml. The resulting mixture was centrifuged at 1,300×g for 15 minutes at room temperature to remove debris and then at 230,000×g for 12 hours at 20° C. Thereafter, a layer containing plasmid DNA was separated from the centrifugation tube by detecting the layer with ultraviolet light. In order to remove ethidium bromide, the thus obtained plasmid DNA was extracted three times with butanol which had been saturated with TE, followed by overnight dialysis against TE at 4° C. The thus dialyzed sample was extracted once with TE-saturated phenol and then twice with a chloroform/isoamyl alcohol system. To this were added 1/10 volume of 3M sodium acetate (pH 5.2) and 2 volumes of ethanol. After standing for 30 minutes at −80° C., the resulting mixture was centrifuged at 12,000×g for 15 minutes at 4° C. The precipitate thus recovered was washed with 70% ethanol, dried and then dissolved in 200 μl of TE. In this manner, about 10 μg of DNA was obtained.

(2) Preparation of Host Cells

Streptomyces lividans 3131 containing pIJ 702 was cultured at 30° C. for 7 days using YEME medium. The resulting culture broth was diluted with YEME medium to a degree of $10^5$ to $10^9$, and a 100 μl portion of each of the thus decimally diluted samples was inoculated on each of five plates containing YEME agar medium (YEME medium supplemented with 1.5% agar). After culturing at 30° C. for 7 days, colonies formed on the plate medium were replicated on YEME agar medium containing 200 μg/ml of thiostrepton making use of RepliPlate ™ Colony Transfer Pad (Takara Shuzo Co., Ltd.), and the thus replicated colonies were cultured again at 30° C. for 7 days. A thiostrepton-sensitive strain *Streptomyces lividans* 3131-TS isolated in this manner was used as the host.

(3) Preparation of *Streptomyces lividans* 3131-TS Protoplasts

The thiostrepton-sensitive strain of *Streptomyces lividans* 3131-TS obtained as in (2) above was cultured at 30° C. for 2 days using the YEME +0.5% glycine medium. A 200 ml portion of the resulting culture broth was centrifuged at 1,300×g for 10 minutes at room temperature, and the cells thus precipitated were suspended in 72 ml of 0.35M sucrose solution. The cell suspension was centrifuged at 1,300×g for 10 minutes at room temperature, and the thus precipitated cells were suspended in 60 ml of buffer solution P containing 1 mg/ml of lysozyme (Sigma Chemical Co.). After incubating at 30° C. for 2.5 hours, the resulting suspension was filtered through absorbent cotton to remove debris. A filtrate thus obtained was centrifuged at 1,300×g for 10 minutes at room temperature, and protoplasts thus precipitated were washed twice with 25 ml of buffer solution P by centrifugation. Thereafter, the thus washed precipitate was suspended in 1 ml of buffer solution P to obtain a protoplast suspension. Buffer solution P used herein was prepared as follows.

| | |
|---|---|
| TES [N-Tris(hydroxymethyl)methyl-2-aminoethane sulfonic acid] | 5.73 g |
| Sucrose | 103 g |
| Magnesium Chloride | 2.03 g |
| Potassium Sulfate | 0.5 g |
| Calcium Chloride | 3.68 g |
| Trace Element Solution* | 2 ml |
| Total | 1 liter (pH 7.4) |
| *Trace Element Solution (per liter) | |
| Zinc Chloride | 40 mg |
| Ferric Chloride | 200 mg |
| Cupric Chloride | 10 mg |
| Manganese Chloride | 10 mg |
| Sodium Tetraborate | 10 mg |
| Ammonium Molybdate | 10 mg |

In this instance, a 1% potassium dihydrogenphosphate solution was separately prepared and a 1 ml portion of the solution was added to 100 ml of buffer solution P prior to use.

(4) Construction of Actinomycetes Expression Type BTG Gene Fragment (Mp-BTGspm)

Since DNA sequencing results indicated that the BTG gene would form a prepro body, it was considered that processing of a precursor into a mature form would be effected smoothly by expressing the gene in *Streptomyces lividans* 3131-TS which belongs to the same actinomycetes family as in the case of the BTG-producing Streptoverticillium sp., rather than expressing it in other microorganisms. As a result, an expression type BTG gene fragment was constructed in the following manner.

i) Preparation of fragment containing signal, pro and structural sequences of BTG gene A fragment containing signal, pro and structural sequences of BTG gene (hereinafter, referred to as "BTGspm fragment") was obtained using PCR technique using a 3.6 Kbp NcoI fragment of BTG gene as a template. Sequences of Primer #3 and Primer #4 used for the PCR procedure were as follows.

Primer #3

5'-ACGAGCTCAAAGGAGTTGCAGGTTTCCATGCGCTAT-3'
      |
      SacI                                    (36 mer)

(SEQ ID NO: 14)

Primer #4

5'-CCGGATCC AGATCT CACATCACGGCCAGCCCTGCTT-3'
     |        |
     BamHI   BglII                           (36 mer)

(SEQ ID NO: 15)

The PCR technique is already described in detail in Example 1 above for the procedures below.

ii) Preparation of fragment of mel (melanin synthesis gene) promoter region

The mel gene was selected as an expression promoter of the BTG gene, and a fragment of mel gene promoter region (referred to as "Mp fragment" hereinafter) was prepared by PCR using pIJ 702 as a template. The Primer #5 and Primer #6 sequences used for the PCR procedures were as follows.

Primer #5

5'-ACGAGCTCGTTGGGTTGACGACCCCG-3'
      |
      SacI                          (26 mer)

(SEQ ID NO: 16)

Primer #6

5'-ACGAATTCTGCAGTTTTCGCACGTGAGCCA-3'
      |       |
      EcoRI   PstI                   (30 mer)

(SEQ ID NO: 17)

iii) Construction of BTG gene fragment (Mp-BTGspm)

Each of the Mp fragment thus amplified by PCR and plasmid pUC 19 was digested with EcoRI and SacI (TOYOBO Co., Ltd.), and digested fragments having appropriate sizes of interest (about 260 bp and about 2700 bp, respectively) were recovered by low melting point agarose electrophoresis. After ligating the thus recovered fragments, *E. coli* DHα was transformed with the resulting ligate in the presence of X-gal and IPTG to isolate an ampicillin-resistant white colony. A plasmid recovered from the colony, in which the Mp fragment was inserted into the EcoRI-SacI site of pUC 19, was designated pUC19-Mp and used in the following procedures.

Each of the BTGspm fragment amplified by PCR in the same manner and the pUC19-Mp thus obtained were digested with BamHI and SacI (TOYOBO Co., Ltd.) and subjected to subcloning. A plasmid in which the BTGspm fragment was inserted into the BamHI- SacI site of pUC19-Mp was designated pUC19-Mp-BTGspm and used in the following procedures.

The plasmid pUC19-Mp-BTGspm thus prepared was treated with PstI and BglII (TOYOBO Co., Ltd.) to obtain a Mp-BTGspm fragment consisting of 1.4 kilo base pairs (Kbp). In these experiments, a DNA Ligation Kit manufactured by Takara Shuzo Co., Ltd. was used.

(5) Incorporation of BTG Gene into *Streptomyces lividans* 3131-TS

The 1.4 Kbp Mp-BTGspm fragment obtained above was ligated with a 5.1 Kbp PstI-BglII fragment of pIJ 702. The ligation was carried out by incubating the following reaction mixture overnight at 4° C.

| 1.4 Kbp Mp-BTGspm Fragment | 8.5 μl (ca. 500 ng) |
|---|---|
| 5.1 Kbp pIJ702 PstI-BglII Fragment | 8.5 μl (ca. 500 ng) |
| 5 units/μl T4 DNA Ligase (Boehringer) | 1.0 μl |
| 10 × Ligation Buffer (Boehringer) | 2.0 μl |

After incubation, *Streptomyces lividans* 3131-TS was transformed with the thus ligated DNA in the following manner.

(a) The following reaction mixture was prepared and the total volume was adjusted to 140 μl.

| DNA Solution | 20 μl |
|---|---|
| *Streptomyces lividans* 3131-TS Protoplasts | 100 μl |
| 0.35 M Sucrose | 20 μl |

(b) A 1.5 ml portion of buffer solution P containing 20% polyethylene glycol 1000 was added to the reaction mixture and mixed gently by pipetting.

(c) The resulting mixture was allowed to remain still for 2 minutes at room temperature.

(d) The mixture was then centrifuged at 1,700×g for 10 minutes at room temperature to collect pellet.

(e) The thus obtained pellet was washed twice with buffer solution P by centrifugation.

(f) The washed pellet was suspended in 1 ml buffer solution P, and a 200 μl portion of the suspension was inoculated on an R-2 medium. In this instance, medium compositions R-2/A and R-2/B as shown below were prepared separately, and the R-2 medium was prepared by mixing these two compositions together with 1% $KH_2PO_4$ solution (1 ml per 200 ml final volume).

| R-2/A (per 1 liter) | |
|---|---|
| Potassium Sulfate | 0.5 g |
| Magnesium Chloride | 20.2 g |
| Calcium Chloride | 5.9 g |
| Glucose | 20.0 g |
| Proline | 6.0 g |
| Casamino Acid | 0.2 g |
| Trace Element Solution | 4 ml |
| Agar | 44.0 g |
| R-2/B (per 1 liter, pH 7.4) | |
| TES | 11.5 g |
| Yeast Extracts | 10.0 g |
| Sucrose | 203 g |

(g) The thus inoculated plates were incubated at 30° C. for 18 hours.

(h) The entire surface of the plate medium was covered with 1 ml of buffer solution P containing 200 μg/ml of thiostrepton and 400 μg/ml of tyrosine.

(i) The resulting plates were further incubated at 30° C. for 7 days to isolate thiostrepton-resistant white colonies. In this instance, a cell containing pIJ 702 in which a foreign DNA fragment was not inserted forms a black colony due to melanin synthesis by the mel gene.

Plasmids were recovered from several white colonies thus isolated, and checked for the presence of inserted BTG gene. A BTG expression secretion vector thus obtained was designated pIJ702-BTG.

(6) Expression of BTG Gene

*Streptomyces lividance* AKW-1 was transformed with the thus obtained BTG gene-incorporated expression vector pIJ702-BTG and the resulting transformant was cultured at 30° C. for 5 days using a medium having the following composition.

| Polypeptone | 2% |
|---|---|
| Soluble Starch | 2% |
| Yeast Extracts | 0.2% |
| $K_2HPO_4$ | 0.2% |
| $MgSO_4$ | 0.1% |
| Adekanol LG126 | 0.05% |
| 50 mg/ml thiostrepton solution | 0.1% |

A 100 ml portion of the thus obtained culture broth was centrifuged at 12,000×g for 10 minutes at 4° C., and the resulting supernatant fluid was concentrated by a factor of about 17 using an ultrafiltration membrane (nominal molecular weight cutoff of 1,000; Amicon Corp.).

Next, the amount of BTG in the thus prepared sample was measured by the EIA (enzyme immunoassay) method making use of an anti-BTG antibody preparation obtained in rabbit using purified BTG. As a result, about 0.1 mg/l of the BTG was detected. In this instance, the EIA was carried out in the following manner.

(a) A 50 μl portion of a sample was mixed with 500 μl of buffer A. After adding a single antibody-linked bead (beads were prepared from polystyrene #80 manufactured by Sekisui) thereto, the mixture was incubated at 37° C. for 30 minutes.

(b) The bead was removed from the thus incubated mixture and washed twice with 10 mM phosphate buffer (pH 7.0).

(c) A 500 μl portion of a β-galactosidase-labeled antibody preparation (50 mu/500 μl buffer A) was added to the thus washed bead and incubated at 37° C. for 30 minutes.

(d) The bead was removed from the thus incubated mixture and washed twice with 10 mM phosphate buffer (pH 7.0).

(e) A 500 μl portion of CPRG was added to the thus washed bead and incubated at 37° C. for 30 minutes.

(f) After terminating the reaction with 2 ml of a stop solution, the absorbance at 575 nm was measured.

| Buffer A | |
|---|---|
| 0.1 M | Sodium Chloride |
| 0.1% | BSA |
| 1 mM | Magnesium Chloride |
| 0.1% | Sodium Azide |
| 10 mM | Phosphate Buffer (pH 7.0) |
| CPRG (per 1 liter, pH 5.0) | |

| -continued | |
|---|---|
| CPRG (chlorophenol red β-D-galactopyranomide, Boehringer) | 1 g |
| BSA | 333.2 mg |
| KH$_2$PO$_4$ | 833.2 mg |
| Na$_2$SO$_3$ | 166.8 mg |
| GH | 333.2 ml |
| GH | |
| 5% | Hydrolyzed Gelatin |
| 0.3 M | Sodium Chloride |
| 1 mM | Magnesium Chloride |
| 0.1% | Sodium Azide |
| 0.1% | BSA |
| 50 mM | Phosphate Buffer (pH 7.0) |
| Stop Solution | |
| 10 mM | EDTA · 2H$_2$O |
| 1% | Galactose |
| 0.1% | Sodium Azide |
| 50 mM | Phosphate Buffer (pH 7.0) |

The recombinant BTG was then analyzed by Western blotting. The Western blotting results are shown in the accompanying FIGURE. Firstly, a sample was treated in the usual way prior to subjecting it to SDS-PAGE. After the electrophoresis, the protein present in the gel was transferred to a membrane (Immobilon ™, Millipore Corp.) using an Electrophoretic Transfer Kit (LKB Instruments, Inc.) under the transfer conditions described in the instructions attached to the kit. The protein-transferred membrane was incubated for 1 hour in 10 ml of a blocking buffer consisting of 20 mM Tris-HCl (pH 7.9) and 5% skim milk and then overnight at 4° C. in 10 ml of a solution of BTG antiserum which has been diluted by a factor of 200 with a rinse buffer consisting of 10 mM Tris-HCl (pH 7.9), 0.15M NaCl, 0.1 mM EDTA (3 Na), 0.25% skim milk and 0.01% NaN$_3$. After washing twice with the rinse buffer (20 ml for each), the thus incubated and washed membrane was incubated at 4° C. for 4 hours in 10 ml of the rinse buffer containing 1 μCi of anti-rabbit $^{125}$I-labeled whole antibody (Amersham). Thereafter, the thus incubated membrane was washed twice with the rinse buffer (20 ml for each), air-dried and then subjected to autoradiography.

As a result, BTG as a mature protein was found at a position of about 37 kilo daltons (KDa), a position equivalent to the molecular weight of the purified BTG, indicating that mature BTG protein was secreted by normal processing in spite of the introduction of a precursor gene into the expression system of BTG gene in *Streptomyces lividans* AKW-1.

EXAMPLE 5

Expression of BTG Gene (Synthetic) in Yeast

For expression of BTG gene in yeast, at a 3' end site of the signal sequence gene in an expression vector the BTG mature gene or with a ligated sequences of a BTG pro-sequence gene and BTG mature gene was inserted.

An *E. coli*-yeast shuttle vector pNJ 1053 which contains a promoter sequence of enolase gene (ENO 1) involved in the glycolytic pathway was used as the expression vector, because this sequence shows a strong promoter activity in yeast. For example, the ENO 1 promoter has been used for the expression of a human lysozyme gene and the like in yeast cells as disclosed for instance by Ichikawa, K. et al. in *Agric. Biol. Chem.*, vol. 53, p. 2687 (1989). This vector is a high copy type (YEp) vector which simultaneously contains pBR322-derived *E. coli* replication origin and ampicillin resistance gene, yeast 2 μm replicatioh origin and LEU 2 gene as a selection marker.

As the signal sequence, a human gastrin signal sequence (Kato, K. et al., *Gene*, vol. 26, pp. 53–57, (1983)) was used. This signal sequence, which consists of 21 amino acid residues and in which the carboxyl terminal side of its 21 position alanine is cut by the action of signal peptidase, has been employed in yeast cells for the expression and secretion of various foreign proteins such as human α-amylase (Sato, T. et al., *Gene*, vol. 83, pp. 355–365, (1989)).

As is known in *Bacillus subtilis*, a pro-sequence which is interposed between a signal sequence and a mature gene sequence assumes to have an important role in the expression of the activity of translated protein (Ikemura, H. et al., *J. Biol. Chem.*, vol. 262, pp. 7859–7864 (1987); and other reports). The term "BTG pro-sequence" as used herein means a sequence of 39 amino acid residues starting from the −39 position lysine to the −1 position proline located downstream of the BTG signal-like sequence as shown in Example 1.

(1) Construction of Mature BTG Expression/Secretion Vector pNJ1053-BTG

A XhoI-HindIII fragment which consists of about 90 base pairs and contains a signal sequence-encoding gene was cut out from a gastrin signal sequence-containing vector (Sato, T. et al., *Gene*, vol. 83, pp. 355–365, (1989)) and inserted into a vector pHSG 396 (Takara Shuzo Co., Ltd.; Takeshita, S. et al., *Gene*, vol. 61, pp. 63–74, (1987)) which had been digested in advance with XhoI and HindIII to obtain a plasmid pHSG396-GS. A HindIII-digested fragment of this plasmid was ligated in series with a synthetic oligonucleotide consisting of about 30 base pairs (bp) as shown below and a PvuII-HindIII fragment (ca. 1 Kb) of the BTG gene chemically synthesized as in Example 2, in order to select a fragment in which mature BTG gene was inserted correctly into a downstream site of the signal sequence gene.

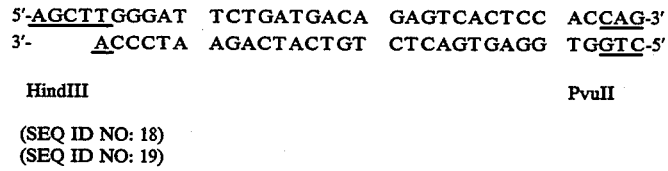

(SEQ ID NO: 18)
(SEQ ID NO: 19)

A SalI-HindIII region upstream of the XhoI recognition site of the thus selected fragment was cut out with corresponding restriction enzymes to obtain a fragment of about 1.1 kilo base pairs (Kbp). Thereafter, a SalI-HindIII region located on a downstream portion of the ENO 1 promoter of the yeast expression vector pNJ 1053 was replaced by the 1.1 Kbp fragment and the resulting plasmid was introduced into *E. coli* JM 109 to recover the titled expression/secretion vector pNJ1053-BTG.

(2) Construction of BTG Pro-sequence—Mature Protein Expression/Secretion Vector pNJ1053-proBTG Firstly, synthesis of a gene which encodes a BTG pro-sequence region was carried out. In this instance, the utilization frequency of codons in *E. coli*, yeast and the like was taken into consideration, and restriction enzyme recognition sites were arranged for use in the ligation of the signal sequence gene and mature gene. That is, as shown below, the 5' end of the pro-sequence gene was arranged with a HindIII cohesive end sequence for use in its ligation with signal sequence gene, and the 3' end with a PvuII blunt end sequence for use in its ligation with the PvuII recognition site of the chemically synthesized BTG gene as in Example 2.

```
      K   R   R   S   P   T   P   K   P   T   A   S   R   R   M   T   S   R   H   Q
5'- AGCTT GGA AGA GAA GAT CTC CAA CTC CAA AGC CAA CTG CTT CTA GAA GAA TGA CTT CTA GAC ACC AA
3'-     A CCT TCT CTT CTA GAG GTT GAG GTT TCG GTT GAC GAA GAT CTT CTT ACT GAA GAT CTG TGG TT
             10          20          30          40          50          60
HindIII R   A   Q   R   S   A   P   A   A   S   S   A   G   P   S   F   R   A   P   D
  AGA GCT CAA AGA TCT GCT CCA GCT GCT TCT TCT GCT GGT CCA TCT TTC AGA GCT CCA GAT
  TCT CGA GTT TCT AGA CGA GGT CGA CGA AGA AGA CGA CCA GGT AGA AAG TCT CGA GGT CTA
           70          80          90         100         110         120

S   D   D   R   V   T   P   P                (SEQ ID NO: 21)
  TCT GAT GAC AGA GTC ACT CCA CCAG -3'           (SEQ ID NO: 20)
  AGA CTA CTG TCT CAG TGA GGT GGTC -5'           (SEQ ID NO: 22)
          130         140
                          PvuII
```

Chemical synthesis of the BTG pro-sequence was carried out by firstly synthesizing a total of 6 oligonucleotide chains, each of which consisting of about 50 bases, as three pairs of double strands using a DNA synthesizer 380A manufactured by Applied Biosystems. The thus chemically synthesized oligonucleotides were phosphorylated, annealed and ligated in that order in the same manner as in the case of the chemical synthesis of BTG gene performed in Example 2. After these reactions, 10% polyacrylamide gel electrophoresis was carried out to recover a DNA fragment of about 150 base pairs from the gel. Next, in the same manner as in section (1) above, a HindIII-digested product of pHSG396-GS, the thus recovered 150 bp synthetic oligonucleotide and the PvuII-HindIII fragment (ca. 1 Kb) of the BTG gene chemically synthesized as in Example 2 were linked to one another in series, and a fragment in which the BTG pro-sequence gene was inserted correctly between the signal sequence and the BTG mature gene was selected. A SalI-HindIII region upstream of the XhoI recognition site of the thus selected fragment was cut out with the corresponding restriction enzymes to obtain a fragment of about 1.2 kilo base pairs (Kbp). Thereafter, a SalI-HindIII region located on a downstream portion of the ENO 1 promoter of the yeast expression vector pNJ 1053 was replaced by the 1.2 Kbp fragment and the resulting plasmid was introduced into *E. coli* JM 109 to recover the titled expression/-secretion vector pNJ1053-proBTG.

(3) Expression of BTG Gene in Yeast

Each of the expression/secretion vectors pNJ1053-BTG and pNJ1053-proBTG thus obtained in the sections (1) and (2) above was incorporated into a host yeast, *Saccharomyces cerevisiae* KSC22-1C (MATa, ssl 1, leu 2, his−, ura 3), by means of an alkali metal treatment (Ito, H. et al., *J. Bacteriol.*, vol. 153, pp. 163–168, (1983)). In this instance, since it is necessary to use a minimum essential medium for the selection and culturing of a clone which has been transformed with a plasmid containing a gene compensating to an auxotrophic mutation, a 0.67% solution of bacto yeast nitrogen base (YNB) available from Difco Laboratories was used as the minimum medium by supplementing it with 2% glucose and, depending on the auxotrophic nature of the host yeast, with 20 mg/l of L-histidine hydrochloride and 20 mg/l of uracil (plus 2% agar in the case of a plate medium). Transformant cells which became Leu+ formed colonies when cultured on the plate medium at 30° C. for 2 to 4 days.

Each transformant containing the expression/secretion vector pNJ1053-BTG or pNJ1053-proBTG was cultured overnight in the minimum essential medium at 30° C. to prevent plasmid deletion and then the resulting culture broth was inoculated (5% inoculum) into 10 ml of the following synthetic medium and cultured at 30° C. for 2 days with shaking.

| Synthetic Medium | |
|---|---|
| YNB | 0.67% |
| Glucose | 8% |
| L-Histidine Hydrochloride | 20 mg/l |
| Uracil | 20 mg/l |
| Casamino Acid (Difco) | 0.5% |

Next, a cell extract was prepared using the glass beads method (Hitzeman, R. A. et al., *Science*, vol. 219, pp. 620–625, (1983)). That is, cells were collected from 10 ml of the cultured broth by centrifugation, washed with sterile water and suspended in 1 ml of a Tris-HCl solution (pH 6.0). A 1 ml volume of glass beads (0.45–0.5 mm in diameter, manufactured by B. Brown) were added to the cell suspension and the mixture was shaked vigorously at 0° to 4° C. for 1 minute on a vortex mixer. The shaking step was repeated three times. After removing the glass beads using a low speed centrifugation, the resulting supernatant was transferred into an Eppendorf tube. The tube was then centrifuged at 12,000 rpm for 5 minutes, and the resulting supernatant was used as a cell extract.

In order to confirm the production of the BTG gene product, an anti-BTG antibody was prepared in a rabbit using purified BTG and Western blotting was carried out using a Vectastain ABC kit (produced by Vector Laboratories, Inc.) in the following manner. A predetermined volume (about 1 μg, as total protein) of each extract of yeast cells containing the expression/secretion vector pNJ1053-BTG or pNJ1053-proBTG was subjected to SDS-polyacrylamide gel electrophoresis and the resulting gel was transferred on a membrane filter (Immobilon, manufactured by Millipore Corp.) to fix the antigen protein on the filter. Thereafter, Western blotting was carried out using the rabbit anti-BTG antibody (1000 times dilution of a stock having an antibody titer of 64) to confirm the product of the BTG gene at the protein level.

In this instance, the protein samples were applied to an SDS-polyacrylamide gel in the following order or lanes.
1: purified BTG (control)
2: extract of yeast cells containing pNJ1053
3: extract of yeast cells containing pNJ1053-BTG (mature BTG gene)
4: extract of yeast cells containing pNJ1053-proBTG (BTG pro-sequence and mature BTG gene)

As a result, colored bands were observed at the same position in lanes 1, 3 and 4. In other words, protein reacted with the anti-BTG antibody was detected in every extract of yeast cells containing the BTG gene at the same position which was equivalent to the molecular weight of the purified BTG.

In this instance, the culture filtrates obtained during the process for the preparation of these cell extracts were also subjected to Western blotting, but no band corresponding to BTG was found. In the case of the yeast cells containing the expression/secretion vector pNJ1053-proBTG in which the BTG pro-sequence and mature BTG gene system had been incorporated, the appearance of a band corresponding to BTG in lane 4 at the same position of the purified BTG indicated that correct processing of the synthetic pro-sequence had occurred in the yeast cells.

While the invention has been described in detail and with reference to specific embodiments thereof, it will be apparent to one skilled in the art that various changes and modifications can be made therein without departing from the spirit and scope thereof.

---

What is claimed is:

1. A chemically synthesized or cloned DNA fragment containing a base sequence which encodes the following amino acid sequence:

```
         10         20
DSDDRVTPPA EPLDRMPDPY 30         40
RPSYGRAETV VNNYIRKWQQ 50         60
VYSHRDGRKQ QMTEEQREWL 70         80
SYGCVGVTWV NSGQYPTNRL 90        100
AFASFDEDRF KNELKNGRPR 110        120
SGETRAEFEG RVAKESFDEE 130        140
KGFQRAREVA SVMNRALENA 150        160
HDESAYLDNL KKELANGNDA 170        180
LRNEDARSPF YSALRNTPSF 190        200
KERNGGNHDP SRMKAVIYSK 210        220
HFWSGQDRSS SADKRKYGDP 230        240
DAFRPAPGTG LVDMSRDRNI 250        260
PRSPTSPGEG FVNFDYGWFG 270        280
AQTEADADKT VWTHGNHYHA 290        300
PNGSLGAMHV YESKFRNWSE
```

```
                310       320
         GYSDFDRGAY VITFIPKSWN
     330
TAPDKVKQGW P
(SEQ ID NO: 1).
```

2. The DNA fragment according to claim 1, wherein the 5' end of said base sequence is further ligated with a base sequence which encodes the following amino acid sequence:

```
-39         -30         -20         -10
  KRRSPTPKP TASRRMTSRH QRAQRSAPAA SSAGPSFRAP
```

(SEQ ID NO: 5).

3. The DNA fragment according to claim 1, wherein the 5' end of said base sequence is further ligated with a base sequence which encodes the following amino acid sequence:

```
-75   -70        -60         -50
 MRYTP EALVFATMSA VYAPPDSCRR PARPPPTMAR
-40         -30         -20         -10
  GKRRSPTPKP TASRRMTSRH QRAQRSAPAA SSAGPSFRAP
```

(SEQ ID NO: 4).

4. The DNA fragment according to claim 1, wherein said fragment contains the following base sequence:

GAT TCT GAT GAC AGA GTC ACT CCA CCA GCT
GAA CCA TTG GAT AGA ATG CCA GAT CCA TAC
AGA CCA TCT TAC GGT AGA GCT GAA ACT GTT
GTC AAC AAC TAC ATT AGA AAG TGG CAA CAA
GTC TAC TCT CAC AGA GAT GGT AGA AAG CAA
CAA ATG ACT GAA GAA CAA AGA GAA TGG TTG
TCT TAC GGT TGT GTT GGT GTT ACT TGG GTT
AAC TCT GGT CAA TAC CCA ACT AAC AGA TTG
GCT TTC GCT TCT TTC GAT GAA GAT AGA TTC
AAG AAC GAA TTG AAG AAC GGT AGA CCA AGA
TCC GGT GAA ACT AGA GCT GAA TTC GAA GGT
AGA GTT GCT AAG GAA TCT TTC GAT GAA GAA
AAG GGT TTC CAA AGA GCT AGA GAA GTT GCT
TCT GTT ATG AAC AGA GCT CTA GAA AAC GCT
CAC GAT GAA TCT GCT TAC TTG GAT AAC TTG
AAG AAG GAA TTG GCC AAC GGT AAC GAT GCT
TTG AGA AAC GAA GAT GCT AGA TCC CCA TTC
TAC TCT GCT TTG AGA AAC ACT CCA TCT TTC
AAG GAA AGA AAC GGT GGT AAC CAC GAT CCA
TCC AGA ATG AAG GCT GTT ATT TAC TCT AAG
CAC TTC TGG TCT GGT CAA GAT AGA TCT TCT
TCT GCT GAT AAG AGA AAG TAC GGT GAT CCA
GAT GCT TTC AGA CCA GCT CCA GGT ACC GGT
TTG GTC GAC ATG TCC AGA GAT AGA AAC ATT
CCA AGA TCC CCA ACT TCT CCA GGT GAA GGT
TTC GTC AAC TTC GAT TAC GGT TGG TTC GGT
GCT CAA ACT GAA GCT GAT GCT GAT AAG ACT
GTT TGG ACC CAT GGT AAC CAC TAC CAC GCT
CCA AAC GGT TCT TTG GGT GCT ATG CAC GTC
TAC GAA TCT AAG TTC AGA AAC TGG TCT GAA
GGT TAC TCT GAT TTC GAT AGA GGT GCT TAC
GTT ATT ACT TTC ATT CCA AAG TCT TGG AAC
ACT GCT CCA GAC AAG GTC AAG CAA GGT TGG
CCA (SEQ ID NO: 2).

5. The DNA fragment according to claim 4, wherein the 5' end of said base sequence is further ligated with the following base sequence:

AAGAGAAGATCTCCAACTCCAAAGCCAACTGCTTCTAGAAGAATGACTTCTAGACA

CCAAAGAGCTCAAAGATCTGCTCCAGCTGCTTCTTCTGCTGGTCCATCTTTCAGAG

CTCCA (SEQ ID NO: 7).

6. The DNA fragment according to claim 1, wherein said fragment contains the following base sequence:

GACTCCGACGACAGGGTCACCCCTCCCGCCGAGCCGCTCGACAGGATGCCCGACCC

GTACCGTCCCTCGTACGGCAGGGCCGAGACGGTCGTCAACAACTACATACGCAAGT

GGCAGCAGGTCTACAGCCACCGCGACGGCAGGAAGCAGCAGATGACCGAGGAGCAA

CGGGAGTGGCTGTCCTACGGCTGCGTCGGTGTCACCTGGGTCAATTCGGGTCAGTA

CCCCACGAACAGACTGGCCTTCGCGTCCTTCGACGAGGACAGGTTCAAGAACGAGC

TGAAGAACGGCAGGCCCCGGTCCGGCGAGACGCGGGCGGAGTTCGAGGGCCGCGTC

GCGAAGGAGAGCTTTGATGAAGAGAAGGGGTTCCAGCGGGCGCGTGAGGTGGCGTC

```
CGTGATGAACAGGGCCCTGGAGAACGCCCACGACGAGAGCGCTTACCTCGACAACC

TCAAGAAGGAACTGGCGAACGGCAACGACGCCCTGCGCAACGAGGACGCCCGTTCC

CCGTTCTACTCGGCGCTGCGGAACACGCCGTCCTTTAAGGAGCGGAACGGAGGCAA

TCACGACCCGTCCAGGATGAAGGCCGTCATCTACTCGAAGCACTTCTGGAGCGGCC

AGGACCGGTCGAGTTCGGCCGACAAGAGGAAGTACGGCGACCCGGACGCTTTCCGC

CCGGCCCCCGGGACCGGCCTGGTCGACATGTCGAGGGACAGGAACATTCCGCGCAG

CCCCACCAGCCCCGGTGAGGGATTCGTCAATTTCGACTACGGCTGGTTCGGCGCCC

AGACGGAAGCGGACGCCGACAAGACCGTCTGGACCCACGGAAATCACTATCACGCG

CCCAATGGCAGCCTTGGTGCCATGCATGTATACGAGAGCAAGTTCCGCAACTGGTC

CGAAGGTTACTCCGACTTCGACCGCGGAGCCTATGTGATCACCTTCATCCCCAAGA

GCTGGAACACCGCCCCCGACAAGGTAAAGCAGGGCTGGCCG
```

(SEQ ID NO: 3).

7. The DNA fragment according to claim 6, wherein the 5' end of said base sequence is further ligated with the following base sequence:

```
ATGCGCTATACGCCGGAGGCTCTCGTCTTCGCCACTATGAGTGCGGTTTATGCACC

GCCGGATTCATGCCGTCGGCCGGCGAGGCCGCCGCCGACAATGGCGCGGGGGAAGA

GACGAAGTCCTACGCCGAAACCTACCGCCTCACGGCGGATGACGTCGCGACATCAA

CGCGCTCAACGAAGCGCTCCGGCCGCTTCGAGCGCCGGCCCGTCGTTCCGGGCCCC

C
```

(SEQ ID NO: 6).

8. An expression secretion vector including the DNA fragment of claims 1, 2, 3, 4, 5, 6, or 7.

9. The expression secretion vector according to claim 8, wherein said vector is pOMPA-BTG.

10. The expression secretion vector according to claim 8, wherein said vector is pNJ1053-BTG.

11. The expression secretion vector according to claim 8, wherein said vector is pNJ1053-proBTG.

12. The expression secretion vector according to claim 8, wherein said vector is pIJ702-BTG.

13. A process for producing transglutaminase which comprises culturing the transformant according to claim 1 and recovering the protein produced.

14. A transformant comprising a host transformed with the expression secretion vector according to claim 8, said host being selected from the group consisting of Escherichia coli, an actinomycete belonging to the genus Streptomyces, and a yeast belonging to the genus Saccharomyces.

15. The transformant according to claim 14, wherein said host is Escherichia coli.

16. The transformant according to claim 14, wherein said host is Escherichia coli JA 221 (FERM BP-3558).

17. The transformant according to claim 14, wherein said host is an actinomycete belonging to the genus Streptomyces.

18. The transformant according to claim 14, wherein said host is Streptomyces lividans.

19. The transformant according to claim 14, wherein said host is Streptomyces lividans 3131-TS (FERM BP-3586).

20. The transformant according to claim 14, wherein said host is a yeast belonging to the genus Saccharomyces.

21. The transformant according to claim 14, wherein said host is Saccharomyces cerevisiae.

22. The transformant according to claim 14, wherein said host is Saccharomyces cerevisiae KSC22-IC (FERM BP-3585).

* * * * *